United States Patent
Blake et al.

(10) Patent No.: US 9,655,532 B2
(45) Date of Patent: May 23, 2017

(54) WEARABLE PHYSIOLOGICAL MONITORING AND NOTIFICATION SYSTEM BASED ON REAL-TIME HEART RATE VARIABILITY ANALYSIS

(71) Applicants: Michael Blake, Tucson, AZ (US); Rodney Kugizaki, Oro Valley, AZ (US)

(72) Inventors: Michael Blake, Tucson, AZ (US); Rodney Kugizaki, Oro Valley, AZ (US)

( * ) Notice: Subject to any disclaimer, the term of this patent is extended or adjusted under 35 U.S.C. 154(b) by 0 days.

(21) Appl. No.: 15/004,345

(22) Filed: Jan. 22, 2016

(65) Prior Publication Data

US 2016/0367157 A1      Dec. 22, 2016

Related U.S. Application Data

(60) Provisional application No. 62/182,261, filed on Jun. 19, 2015.

(51) Int. Cl.

| | |
|---|---|
| *A61B 5/0428* | (2006.01) |
| *A61B 5/0456* | (2006.01) |
| *A61B 5/024* | (2006.01) |
| *A61B 5/0408* | (2006.01) |
| *A61B 5/0452* | (2006.01) |
| *A61B 5/0205* | (2006.01) |
| *A61B 5/08* | (2006.01) |
| *A61B 5/021* | (2006.01) |
| *A61B 5/00* | (2006.01) |

(Continued)

(52) U.S. Cl.
CPC .......... *A61B 5/02405* (2013.01); *A61B 5/021* (2013.01); *A61B 5/02055* (2013.01); *A61B 5/0452* (2013.01); *A61B 5/0456* (2013.01); *A61B 5/04085* (2013.01); *A61B 5/053* (2013.01); *A61B 5/08* (2013.01); *A61B 5/1118* (2013.01); *A61B 5/6831* (2013.01)

(58) Field of Classification Search
CPC ........................... A61B 5/0456; A61B 5/0468
See application file for complete search history.

(56) References Cited

U.S. PATENT DOCUMENTS

| | | | | |
|---|---|---|---|---|
| 5,280,792 A | * | 1/1994 | Leong | ................ A61B 5/04525 |
| | | | | 128/925 |
| 5,411,031 A | * | 5/1995 | Yomtov | ............... A61B 5/0031 |
| | | | | 600/519 |

(Continued)

OTHER PUBLICATIONS

Malik, Marek, Heart rate variability, Standards of measurement, physiological interpretation, and clinical use, European Heart Journal (1996) 17,354-381.

(Continued)

*Primary Examiner* — Kennedy Schaetzle

(57) ABSTRACT

Methods, devices, and systems for monitoring heart rate variability (HRV). The HRV monitoring systems and devices are adapted to give immediate feedback to the subject concerning their current condition and any pertinent changes in their condition. The HRV monitoring systems and devices detect, analyze, and assess HRV against a pre-determined application or user need. They also have the ability to provide real time notifications based on the system's assessment of a user's heart HRV and changes in the HRV.

1 Claim, 16 Drawing Sheets

(51) Int. Cl.
*A61B 5/11* (2006.01)
*A61B 5/053* (2006.01)

(56) References Cited

U.S. PATENT DOCUMENTS

| | | | | |
|---|---|---|---|---|
| 5,682,901 A * | 11/1997 | Kamen | ................ | A61B 5/0468 600/519 |
| 6,212,427 B1 * | 4/2001 | Hoover | ................ | A61B 5/0006 600/515 |
| 6,480,733 B1 * | 11/2002 | Turcott | ................ | A61B 5/0002 600/509 |
| 7,460,899 B2 | 12/2008 | Almen | | |
| 2004/0049120 A1 * | 3/2004 | Cao | ..................... | A61B 5/0456 600/521 |
| 2005/0177051 A1 | 8/2005 | Almen | | |
| 2005/0251051 A1 * | 11/2005 | Pougatchev | ....... | A61B 5/02405 600/485 |
| 2006/0151210 A1 * | 7/2006 | Hirai | ..................... | H05K 3/365 174/495 |
| 2007/0021815 A1 * | 1/2007 | Kaiser | ................... | A61B 5/024 607/141 |
| 2008/0082001 A1 * | 4/2008 | Hatlestad | ........... | A61B 5/02405 600/481 |
| 2010/0049070 A1 | 2/2010 | Kao | | |
| 2010/0113889 A1 * | 5/2010 | Ghanem | ............ | A61N 1/36564 600/301 |
| 2010/0125217 A1 | 5/2010 | Kuo | | |
| 2010/0204597 A1 * | 8/2010 | Ghanem | ................ | A61B 5/046 600/512 |
| 2010/0274144 A1 * | 10/2010 | Hu | ..................... | A61B 5/02405 600/500 |
| 2010/0274308 A1 * | 10/2010 | Scott | .................. | A61N 1/36135 607/9 |
| 2011/0184298 A1 * | 7/2011 | De Marchena | .... | A61B 5/02405 600/509 |
| 2011/0245633 A1 | 10/2011 | Goldberg | | |
| 2011/0270346 A1 * | 11/2011 | Frei | ..................... | A61B 5/0245 607/45 |
| 2013/0184517 A1 | 7/2013 | Collier | | |
| 2014/0073982 A1 | 3/2014 | Yang et al. | | |
| 2014/0135631 A1 | 5/2014 | Brumback | | |

OTHER PUBLICATIONS

W.-C. Fang et al. Expert Systems with Applications 40 (2013) 1491-1504.

Jongyoon Choi et al., Using Heart Rate Monitors to Detect Mental Stress, 2009 Body Sensor Networks 219-223.

* cited by examiner

| HRV Measurement | Description | Value basis | Applied affects, Primary Threshold, Example applicability |
|---|---|---|---|
| SDNN | Standard deviation of all NN intervals | Time domain, statistical | Time and sampling dependent<br>Absolute value - msec<br>Est high freq variations in heartrate, overall HRV<br>e.g., Effects of pollution |
| RMSSD | Sq root of mean squared differences of successive NN intervals | Time domain, statistical | Time and sampling dependent<br>Absolute value - msec<br>Est of short term components of HRV<br>e.g., Stress |
| SDSD | Std deviation of differences between adjacent NN intervals | Time domain, statistical | Time and sampling dependent<br>Absolute value - msec<br>e.g., Driver fatigue |
| SDANN | Std deviation of averages of NN intevals – 5 minute segments | Time domain, statistical | Time and sampling dependent<br>Absolute value - msec<br>Est of long term components of HRV with Approx correlation to ULF<br>e.g., Cardiac arrhythmia |
| TINN | Triangular interpretation of NN integral histogram – base width of triangle | Time domain, geometric | Relative insensitivity to NN intervals<br>Absolute value – msec<br>Good for large time frames<br>e.g., Stress |
| pNNx | NN count divided by total NN interval | Time domain, statistical | Rate of change – percentage<br>e.g., Food allergies |
| VLF | Power in Very low frequency range | Frequency domain, spectral | Absolute value – $M\text{-}S^2$<br>$\leq 0.04$ Hz<br>e.g., Asthma |
| LF | Power in Low frequency range | Frequency domain, spectral | Sensitive to 'stationarity'<br>Absolute value – $M\text{-}S^2$ and N.U. (LF Normalized)<br>0.04 – 0.15 Hz<br>e.g., Stress |
| HF | Power in High Frequency range | Frequency domain, spectral | Sensitive to 'stationarity'<br>Absolute value – $M\text{-}S^2$ and N.U. (HF Normalized)<br>0.15 – 0.4 Hz<br>e.g., VOC exposure, Epilepsy |

FIG. 2

| HRV Measurement | Description | Value basis | Applied affects, Primary Threshold, Example applicability |
|---|---|---|---|
| LF/HF | Ratio of LF to HF, indication of distribution of power in frequency domain | Frequency domain, spectral | Sensitive to 'stationarity' Absolute value (also applies to normalized values) e.g., Driver fatigue |
| SD1 | SD of axis of Poincare plot perpendicular to the line of identity | Nonlinear, Scatter plot | Absolute value -- msec e.g., lactate threshold |
| SD2 | SD of axis of Poincare plot parallel to the line of identity | Nonlinear, scatter plot | Absolute value -- msec |
| SD1/SD1 | Ratio of SD1 to SD2 -- indicates level of spread in pointcare plot | Nonlinear, scatter plot | Ratio, absolute value e.g., postoperative ischemia |
| Hilbert Transform | Use of a HT is described as an analytical approach to enhance spectral analysis | Nonlinear/ fractal | Absolute value Extraction of HF and LF coupling components to inhalation e.g., Apnea |
| ApEn | Approximate Entropy determination of variability in periodic events | Non-linear, Entropy | Absolute value e.g., Mood changes, stress, cardiac health |
| SampEn | Sample Entropy | Non-linear, Entropy | Absolute value e.g., fainting, bipolar, cardiac health |
| FuzzEn FuzzMEn | Fuzzy Entropy Fuzzy Measure Entropy | Non-linear, Entropy | Improvements over other entropy methods Absolute value e.g., Cardiac health |

Note: The term "NN" is used in place of RR to emphasize the fact that the processed beats are "normal" beats.

FIG. 2 continued

| Application | Parameter | Criticality |
|---|---|---|
| Real Time Lactate Threshold | SDNN | Indication for LT :< 3.0, must be real time |
| | Heartrate | Must relate to conditions for user that indicate level of exertion around lactate threshold |
| | Respiration | Increased respiration consistent with elevated activity |
| | Motion, activity | Consistent with elevated activity |
| Elevated Stress | RMSDD | Depressed value indicates of other conditions exist<br>Extreme benefit if available for short term determinations |
| | Conditions | Characterization of conditions that induce stress |
| Driver Fatigue or drowsiness | SDSD | Real time required for effective mitigation |
| | LF/HF | Real time required for effective mitigation |
| | Motion/activity | Baseline motion/activity dynamically established for comparison |
| | Heartrate | Real time required, must relate to basel rate determined for user and activity |
| | Barometer | Indicates altitude changes of user |
| Food allergies/ sensitivities | pNNx | Preview response to intake previews external response<br>Short term or real time determinations provide for easy mitigation of condition |
| | History | Patient history of severe allergic reaction |
| | Clinical testing | Patient testing of severe allergic reaction |
| Sleep Apnea | Hilbert Transform | Short term determination needed for real (short) time correction |
| | Motion | Motion consistent with sleeping or resting |
| | Temperature | |
| | Respiration | Respiration consistent with sleeping or resting, indications of apnea events can be derived from analysis or optionally monitored independently |
| | Conditions | Subject sleeping or intending |
| Mood changes, stress, depression | ApEn | Long term acceptable for trending, short term very beneficial for corrective action |
| | Indications | Diagnostic pathway concerns for depression |
| | Patient actions | Clinical monitoring of patient responses over time |

FIG. 18

| Application | Parameter | Criticality |
|---|---|---|
| Mental Bipolar | SampEn | |
| | Indications | Diagnostic pathway concerns for depression |
| | Patient actions | Clinical monitoring of patient responses over time |
| Cardiac health maintenance | HRV indications SD1/SD2 | Reduced HRV from healthy baseline Overall HRC response over time Long term assessment acceptable |
| | Indications | Prior cardiac events, surgery, treatment, diagnosis |
| Hypertension | LF | Depressed circadian rhythm of LF Short term assessment very desirable for corrective action |
| | Indication | Known hypertension indication |
| Congestive heart failure | Spectral power | All frequencies SP lower, especially > 0.04Hz Short term or real time very desirable for corrective action |
| | LF/HF | Increased LF/HF ratio |
| | Indication | Known CHF indication |
| Sudden death or cardiac arrest | SDNN | Variation (short term and long term), frequency dependent, indicates increased risk of SD Low SDNN index indicates increased risk Real time essential for corrective action |
| | HF | Lower HF power indicates risk of SD |
| Post operative Ischemia | SD1/SD2 | Overall HRV response over time |
| | Indications | Clinical event (e.g., cardiac surgery) |
| Epileptic event onset | LF/HF and SD1/SD2 | Short term or real time essential for corrective actions |
| Recovery from concussive event in sports | RMSSD | Long term baseline required for acceptable for assessment Short term response useful, long term response indicates recovery |

FIG. 18 continued

WEARABLE PHYSIOLOGICAL MONITORING AND NOTIFICATION SYSTEM BASED ON REAL-TIME HEART RATE VARIABILITY ANALYSIS

CROSS REFERENCE

This application claims priority to U.S. Provisional Patent Application No. 62/182,261, filed Jun. 19, 2015, the specification(s) of which is/are incorporated herein in their entirety by reference.

FIELD OF THE INVENTION

The present invention relates to methods, systems, and devices for real-time monitoring of heart rate variability (HRV), more particularly to HRV monitoring systems and devices that are adapted to give immediate feedback to the subject concerning their current physiological condition and any pertinent changes in their physiology.

BACKGROUND OF THE INVENTION

Heart Rate Variability (HRV) has been widely used as a scientific measurement for monitoring the physiology of both human and animal subjects. HRV is the physiological characteristic of the variation in timing between heartbeats. The heartbeat originates in specialized tissue in the heart called the sino-atrial (SA), continuously generating an electrical impulse that spreads throughout the heart muscle. This initiates process of heart muscle contraction, a well-synchronized pump that sequentially constricts all 4 chambers of the heart (two atria and two ventricles.)

The SA node signals (approximately 100-120 impulses per minute when the heart is at rest) are regulated by the autonomic nervous system (ANS) by inhibiting some of the electrical impulses. The net effect results in a normal resting heart rate (in healthy individuals) of about 55 to 70 beats per minute (at rest). This autonomic nervous system is that part of the nervous system that is not under conscious control. It controls the organs and systems of the body that are rhythmic, regular and automatic such as breathing, digestion and heart rate. There are two branches of the autonomic nervous system: sympathetic and parasympathetic.

The sympathetic nervous system provides the basal heartbeat (HB) rhythm based on overall need. This response of the heart rate to normally encountered levels of sympathetic stimulation is modulated by parasympathetic stimulation. This heartbeat response to the parasympathetic nervous system, in contrast to the sympathetic nervous system, occurs rapidly and frequently. The deceleration of the heartbeat is almost instantaneous. It only takes 1 or 2 heartbeats to see these changes take place, slowing the heart rate.

HRV analysis can be used in both clinical and non-clinical applications for a diverse range of evaluations. In healthy individuals, the HR is variable. It fluctuates and generally, greater variability (or HRV) correlates with better health. Higher HRV indicates a healthy autonomic nervous system, and in particular, healthy balance between the sympathetic and parasympathetic systems. A decreased HRV is an early, accurate indicator that the autonomic nervous system is out of balance. The lower the HRV, the greater the imbalance in autonomic control and the greater the likelihood of poor health, both now and in the future.

Clinical applications for HRV analysis are related to cardiac health, and are indications that are shown to directly relate to health changes with many chronic and critical health conditions. Included are, but not limited to, risk of a cardiac event, occurrence of diabetes, episodic and chronic mental health conditions, sleep apnea, SIDS, exposure to and incidence of allergic reactions.

In non-clinical applications, it has been shown that HRV is effective in indicating a variety of physiological conditions. During vigorous exercise, HRV has been shown to be a marker for entering lactate threshold or anaerobic metabolism. Further, it is shown to be an indicator of physical fatigue, exercise capacity, endurance, and overall fitness. Application has been found to be useful in assessing physiological-behavioral conditions, such as stress in trainee stock market traders and driver fatigue.

There are several ways to measure and analyze HRV. Heart rate signals are obtained through electrocardiogram (ECG) or by pulse wave measurement called "Photoplethysmography" (PPG). The most accurate clinical determination of HRV is derived from measuring the duration of the intervals between contractions of the heart, called interbeat intervals, on ECG (or EKG). In contrast, PPG is less invasive, simpler to apply, and can conveniently access capillaries in a fingertip or the earlobe. Using differential light absorption characteristics and an optical sensor, PPG detects changes in the pulse waves generated by blood flow through the microcirculation. In this way an accurate estimate of HRV can be obtained.

The present invention features system, devices, and methods for real-time HRV monitoring. The HRV systems and devices of the present invention are adapted to give immediate feedback to the subject concerning their current physiological condition and any pertinent changes in their physiology.

A few studies that outline some applications of HRV benefiting from real-time feedback include, but are not limited to clinical applications with real time relevance such as anticipation of mood changes in patients with Bipolar Disorder, alerting the onset of infant physiological dysfunction during sleep, early warning of epileptic seizure, food allergy alerting, and sleep apnea; and non-clinical applications with real time relevance such as predicting the onset of lactate threshold in endurance athletes, warning of physiological effects of pollution, particularly volatile organic compounds (VOCs), alerting the onset of driver fatigue, and monitoring professionals in high stress occupations (e.g., air traffic controllers). These scenarios and many others may benefit from the accurate monitoring, analysis and real time alerting, to a relevant change in physiology as indicated by a change in HRV.

SUMMARY OF THE INVENTION

The present invention features techniques, systems, devices, and methods for the determination, analysis and feedback of HRV to users on a real-time basis. In addition to the detection, analysis and assessment of HRV against a pre-determined application or user need, it has the ability to provide real time notifications, based on the system's assessment of a user's heart rate variability and in particular, changes in heart rate variability, which may be pertinent to a specific application of this invention. This invention may further help a user to take appropriate action based on his/her specific needs.

One aspect of this invention is to provide novel systems, methods and devices for the monitoring and the assessment of the impact of HRV when incorporated with other relevant factors, historical baselines and temporal changes. Further, such temporal changes, of either or both HRV and other factors, are assessed for the providing of significant indication of occurring or impending clinical or non-clinical conditions for a user.

In some embodiments, the systems, devices, and methods of the present invention utilize EKG and/or, e.g., PPG to determined HRV to monitor and assess potential differential in cardiac excitation and response as an indication of occurring or impending clinical or non-clinical conditions for a user. Such a differential assessment may provide insight into the body's physiological response to the autonomous nervous system input to cardiac function driven by psychophysiological input. Monitoring of such response over time may provide potential insight into cardiopulmonary performance and change.

The present invention also provides for the integrated, in situ, real-time, direct feedback of the results of the above-mentioned HRV incorporated assessment or assessments to the user. Such feedback may be useful in informing the user of impending or occurring conditions of high interest on an immediate basis. This feedback may provide significant insight that a user can utilize in their actions, including, but not limited to, health conditions, exercise activities and impactful stress related environments.

According to one embodiment, the invention features a wearable device for real-time detection, analysis and application of heart rate variability (HRV). The device may comprise a chest strap integrated with one or more strap electrodes to detect a plurality of consecutive QRS waves and a battery-powered and self-contained processing circuit. The circuit may comprise a microprocessor operatively coupled to the one or more electrodes and configured to receive at least one additional input unrelated to the QRS waves detected by the strap electrodes, an ECG analog front end circuit coupled between the microprocessor and at least one strap electrode to provide a signal gain control to a strap electrode output such that the microprocessor receives signals with a desired amplitude, a non-volatile memory storing computer-readable instructions, and a notification means to receive a real-time notification to generate a user alert. The notification means may be a haptic indicator, an audio indicator or a visual indicator. When the computer-readable instructions are executed by the microprocessor, the microprocessor can perform operations comprising detecting a rising edge or a declining edge of an R-wave from the each of the QRS waves; triggering an interrupt when the rising edge or the declining edge crosses a trigger point, the trigger point for interrupt triggering being predetermined or dynamically adjusted value; recording a time value each time when the interrupt is triggered; determining an RR interval each time when the time value is recorded; generating a temporal RR interval array, the RR interval array being stored within the memory and comprising a plurality of determined RR intervals; generating an HRV measurement based on the temporal RR interval array; and comparing the generated HRV measurement to an HRV threshold and outputting a real-time notification when the HRV threshold is reached. The HRV threshold can be determined at least by the additional input unrelated to the QRS waves.

As used herein, the trigger point is the voltage level at which the R wave triggers an interrupt.

As used herein, the HRV threshold is the level the selected HRV measurement crosses in order to generate an alert.

As used herein, the RR interval is the time between two consecutive R-waves (usually expressed in milliseconds).

According to another embodiment, the invention features a method for real-time detection, analysis and application of heart rate variability (HRV) using a wearable device. The method may comprise detecting a plurality of consecutive heart-beat related waves using one or more electrodes integrated within the wearable device, detecting a specific wave characteristic from the each of the plurality of heart-beat related waves, triggering an interrupt when the detected specific wave characteristic crosses a trigger point, recording a time value each time when the interrupt is triggered, and determining an interval from the recorded time value. The trigger point may a predetermined value or a dynamically set value. The trigger point may be based on at least one additional input unrelated to the plurality of consecutive heart-beat related waves. The additional input can be a respiration rate, a blood pressure value, a body temperature, a level of physical motion or a level of electrodermal activity (EDA). In one embodiment, the heart-beat related waves are QRS waves. The specific wave characteristic is a rising edge or a declining edge of an R wave within each QRS wave. The interval is an RR interval.

In one aspect, the method may further comprise generating a temporal RR interval array, the RR interval array comprising a plurality of determined RR intervals, generating an HRV measurement based on the temporal RR interval array, and comparing the generated HRV measurement to an HRV threshold and outputting a real-time notification when the HRV threshold is reached. The HRV threshold can be determined by the at least one additional input unrelated to the plurality of consecutive heart-beat related waves, or it can be obtained from pre-stored values or a dynamically determined value calculated in real time.

According to a further embodiment, the invention features a method for ectopic beat detection and heart, rate variability (HRV) determination. The method may comprise retrieving an array comprising a plurality of consecutive RR intervals, implementing a validity check for each of the plurality of consecutive RR intervals, wherein any of the RR intervals that fail the validity check are discarded during the validity check, implementing an ectopic heartbeat identification for the plurality of consecutive RR intervals after the validity check, replacing RR intervals being identified as ectopic heartbeats by a predetermined value or interval values interpolated between adjacent RR interval values passing the validity check, forming a resulting RR interval array with all ectopic heartbeats replaced and calculating an HRV measurement based on the resulting RR interval array.

In some embodiments, the method may further comprise comparing the calculated HRV measurement to an HRV threshold and generating a real-time notification when the calculated HRV measurement reaches or surpasses the HRV threshold. The HRV threshold may be determined by at least one additional input unrelated to the RR intervals. In other embodiments, the method may further comprise transmitting the real-time notification via a communication interface.

In one aspect, the ectopic heartbeat identification may comprise calculating three adjacent heartbeat differences from the plurality of consecutive RR intervals after the validity check, each heartbeat difference being calculated from the difference of two adjacent RR intervals, implementing a threshold test for each of the three adjacent heartbeat differences against a difference threshold, implementing a change direction test for the three adjacent heartbeat differences if all the three adjacent heartbeat differences are above the difference threshold, and identifying the RR intervals related to three adjacent heartbeat differences as ectopic heartbeats if the three adjacent heartbeat differences are non-monotonic. The difference threshold may be a predetermined value or a user settable parameter.

In another aspect, the validity check may comprise checking whether each RR interval is within a time range, which may be between about 250 millisecond (ms) to 1400 ms. In another aspect, the validity check may comprise checking whether each RR interval is within a window around a mean value of a local RR interval dataset.

While there are many configurations and implementations of HRV analytical systems, this invention provides unique improvements and capabilities offering significant advantages over existing systems.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 2 is a table showing exemplary HRV measurements and associated sample applications involving each specific measurement. Each one of these calculations yields a single measurement. In steady state conditions, these measurements remain fairly constant, but can change with changes in the physiology of the subject. For example, if there is a rapid increase in the value of HF preceding an epileptic seizure, or during exercise, the subject crosses his or her lactate threshold as the value of SD1 drops below 3.0.

FIG. 18 is a table of HRV applications, associated parameters and relevant criticality.

One skilled in the art will recognize that various implementations and embodiments of the invention may be practiced in accordance with the specification. All of these implementations and embodiments are intended to be included within the scope of the invention.

DESCRIPTION OF PREFERRED EMBODIMENTS

In the following description, for the purpose of explanation, specific details are set forth in order to provide an understanding of the present invention. The present invention may be practiced without some or all of these details. The embodiments of the present invention described below may be incorporated into a number of different electrical components, circuits, devices, and systems. Structures and devices shown in schematic diagrams are illustrative of exemplary embodiments and are not to be used as a pretext by which to obscure broad teachings of the present invention.

When the specification makes reference to "one embodiment" or to "an embodiment", it is intended to mean that a particular feature, structure, characteristic, or function described in connection with the embodiment being discussed is included in at least one contemplated embodiment of the present invention. Thus, the appearance of the phrase, "in one embodiment," in different places in the specification does not constitute a plurality of references to a single embodiment of the present invention.

The present invention features methods, devices, and systems for monitoring heart rate variability (HRV). For example, the present invention features an improved system to provide real time alerts to a user based on that user's heart rate variability and in particular, changes in heart rate variability that are pertinent to a specific application of need of the user. The system may be configured such that it helps a user to take appropriate action based on their specific needs and application, on a real time basis, in a wide range of environments.

Figure 1:
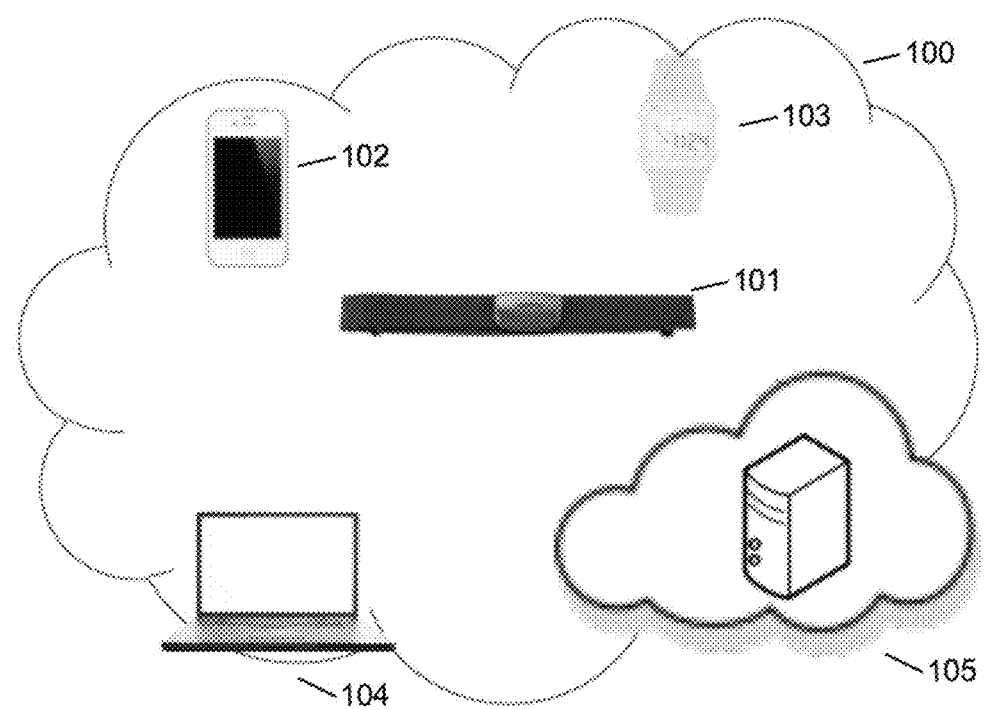
FIG. 1 shows a system diagram of an example of a wearable physiological monitoring and notifying system.

FIG. 1 shows a system diagram of an example of a wearable physiological monitoring and notifying system 100. The system may be configurable in a wide range of ways such that it can be optimized for a user's needs, their use environment and conditions of use. The system comprises a wearable device (Wearable Physiological Monitor—WPM) 101 and associated system components (e.g., a cloud storage and computing components, a computing component, a cell phone component, a wrist display and computing component). In some embodiments, the device 101 that may be completely self-contained and may provide for the detection, analysis and user specific assessment of HRV for a specific application. Such a device may be inconspicuously worn by the user, may be completely portable, may be untethered to any external device, and may be battery powered.

Depending upon the user's needs, environment of use and requirements for connection to external sub-systems, the system may be comprised of a variety of components. Central to this system is the device 101, which provides detection, analysis, assessment and user feedback for user specified conditions for a specified application. The device 101 may couple to a cellular phone component 102, a personal computing component 104, a cloud based storage and computing component 105, and/or a computing wrist display or smart watch component 103. The system may comprise a single, all or any combination of said components to best fulfill user needs.

In some embodiments, the device 100 and, as configured, its associated system components, are capable of supporting all system functions, including the detection of a heart signal, analysis of heartbeat, analysis of HRV, assessment of HRV and at least one other parameter in association with pre-specified user needs and application, and the immediate, real time notification, to the user, of suitable alerts, updates and/or status, and data transfer, alerting or status between any specific or all system components as required.

In some embodiments, the present invention provides, within the system, the ability to detect, measure, and utilize key parameters in the context of the specific user need and application. These parameters include, but are not limited to, motion (e.g., body motion of the user wearing the device), special orientation, barometric pressure (to determine the altitude of the user wearing the device), temperature (to determine the temperature of the user wearing the device and/or the temperature of the environment), and location (to determine the geographic or relative location of a user utilizing the system).

By incorporating the above monitoring into the system, the system can incorporate specific parameters that provide enhanced real time assessment of the impact of HRV for a user specified application. As a summarization of possible parametrics obtainable from analysis of HRV and sample associated applications, refer to table FIG. 2.

The Device

Figure 3:
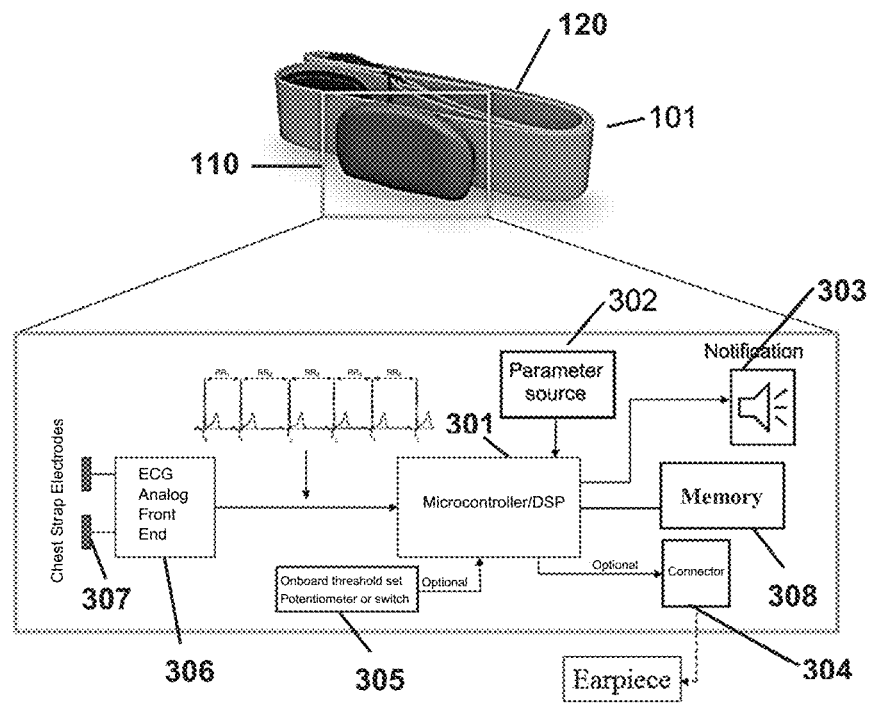
FIG. 3 shows an example of a wearable HRV monitoring device (e.g., compact, integrated, portable, battery powered, etc.).

Referring to FIG. 3, in one embodiment of the device 101, the device is compact, battery powered, wearable, and portable. It may be a user worn device, comprising a chest strap 120 and a self-contained processing circuit 110. The self-contained processing circuit 110 comprises a memory 308 and a microprocessor 301, which couples to at least one strap electrode 307 and functions to extract the inter-beat intervals of the heart, and using these data to calculate heart rate variability, and provide a real time notification to the user via a notification means 303. The notification means 303 may be a speaker or a motion-generating component (such as a vibrator) to arise user attention. In some embodiments, the microprocessor 301 also couples to at least one other parameter source 302 and generate the real time notification based on both the calculated heart rate variability and the at least one parameter source 302. The microprocessor 301 may be a microcontroller, a digital signal processing (DSP) circuit, a programmable logic circuit, a CPU, etc. The memory 308 is a non-volatile computer stage to store computer readable logic/control codes (or instructions) and to store computer generated data. In some embodiments, the microprocessor 301 and the memory 308 are integrated into one integrated circuit.

In some embodiments, the self-contained processing circuit 110 further comprises an onboard threshold set potentiometer (or adjusting switch) 305 coupled to the microprocessor 301. The potentiometer (or adjusting switch) 305 receives user inputs for the microprocessor 301 to calculate HRV measurement accordingly. The user inputs may be an exercise status input, a health status input, etc.

In some embodiments, the self-contained processing circuit 110 further comprises an optional connector 304 coupled to the microprocessor 301, which provides the real time notification to the user through the connector 304 and an external earpiece coupled to the connector.

In some embodiments, the self-contained processing circuit 110 further comprises an ECG analog front end circuit 306 coupled between the microprocessor 301 and the at least one strap electrode 307. The front end circuit 306 may provide a necessary signal gain control to the strap electrode output such that the microprocessor 301 receives signals with desired amplitude.

The principles of ECG waveform detection using a conductive chest strap have been demonstrated in many devices. Although such prior methods are an effective approach, it is one subject of this invention, utilizing a design for the detection and capture of the EKG signal (the QRS complex), to provide a marked improvement over existing methods. These improvements account for greater capture efficacy and more responsive adaptation to unusual circumstances, such as a leads off situation, while maintaining the integrity of the dataset used for calculation of the HRV measurement(s).

Although the wearable device is shown in FIG. 3 with a chest strap 120, it is understood that other variations may be applicable to the device as well. Such variations could be in the form of, but not limited to, a watch, self-adhesive patch, armband, bra, belt, etc. The strap electrode 307 may be integrated into the chest strap 120 such that the electrode may be disposed at the right position when the device is worn by the user.

Figure 4:
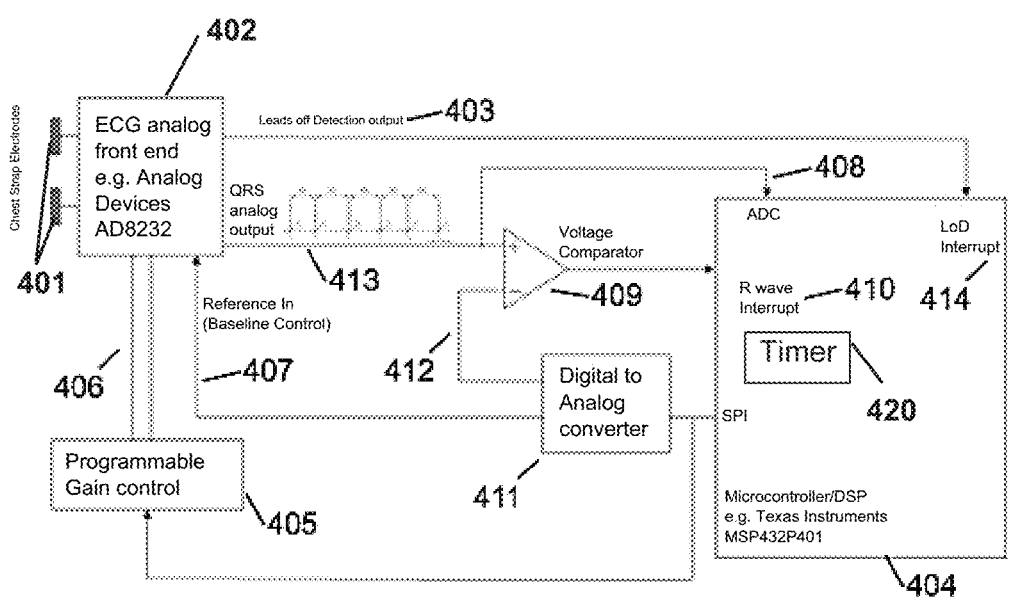
FIG. 4 shows a detailed block diagram of the front-end detection in a HRV device of the present invention.

FIG. 4 shows a detail schematic view of the front-end detection in an embodiment of the present invention. Referring to FIG. 4, two chest strap electrodes 401 are coupled to an ECG analog front end (AFE) integrated circuit 402, such as an Analog chip AD8232. In some embodiments, the AFE 402 contains an internal amplifier to output a conditioned QRS signal 413 comprising multiple QRS complexes to a voltage comparator 409.

In some embodiment, the AFE integrated circuit 402 is configured to output a Lead off Detection (LoD) signal 403 when one or both of the ECG electrodes have been disconnected from the user, thereby compromising the integrity of the ECG data. The LoD signal 403 is coupled to an interrupt input pin 414 of the microcontroller 404. The microcontroller 404 can then activate a 'Fast Restore' feature of the AFE 402 in order to reset the internal filters so that the AFE is reconfigured to immediately detect a new R wave. The microcontroller 404 may also use this information to identify, reject or correct the resulting erroneous RR interval data. Additionally, an internal timer 420 in the microcontroller 404 can monitor the LoD 403 and in event that the leads are off longer than a threshold (a long period of time, such as 15 seconds), enable the microcontroller 404 to enter a low power sleep mode with assumption that the user has removed the device.

In some embodiments, in order to optimize the performance of the AFE 402, the microcontroller 404 may adjust the output gain of the AFE 406 to minimize saturation via a programmable gain control 405. Additionally, the microcontroller 404 can adjust the reference level of the AFE instrumentation amplifier 407 in order to optimize the average level of the R pulse baseline. This can be achieved by monitoring and averaging the QRS signal 408 using an ADC and adjusting the reference-in voltage 407 to maintain a very stable baseline.

Traditionally, the QRS signal is sampled by an analog to digital converter within the microcontroller and peak detection algorithms are executed in the microcontroller to determine the duration of the RR interval. This approach requires signal processing to obtain sufficient resolution and accuracy in determining the specific heartbeat timings and consequently duration of the RR intervals.

It is an object of this invention, in some embodiments, to employ an analog comparator 409 to detect a specific desired wave characteristic and use that detection event to directly trigger an interrupt 410 on the signal processor. The specific wave characteristic may be, but is not limited to, the steep rising edge of the R wave, the peak of the R wave, or the steep declining edge of the R wave complex. Each may be used to directly trigger an interrupt on the microcontroller, with each embodiment having its own characteristics. Combinations of specific wave characteristics are as well possible and it is not meant to, within this invention, to limit the use of and the combinations of wave characteristics for this detection.

A DAC 411 connected to the microcontroller may be used to actively set (or dynamically adjust) the threshold 412 based on the magnitude variation of the R wave between different users or historic data stored within the memory 308. The threshold 412 is used to compare to the conditioned QRS signal 413 by voltage comparator 409. When the conditioned QRS signal 413 reaches the threshold 412, the voltage comparator 409 outputs an interrupt signal 410 to the microcontroller 404. While FIG. 4 shows discrete external components, this is not meant to limit a desired embodiment, as this capability may be discrete or integrated into the microcontroller. It is herein provided for greater clarity of explanation.

The interrupt 410 is used by the microcontroller to obtain a time value from a timer 420 that was reset on the last occurrence of a valid interrupt. The obtained time value is then the most recent RR interval. This direct and temporal determination of the RR interval for HRV provides a highly accurate determination of the RR interval while lowering power requirements, computational requirements, memory storage and timing limitations for computationally intense digitizing/analysis methods. The obtained RR interval array is stored within the memory 308 (not shown in FIG. 4) for further analysis and history data output when applicable. The precision and accuracy of this determination is only limited by the timing capabilities of the microcontroller and is often provided with sub-millisecond resolution and accuracy.

By virtue of the stability provided by the above described technique, it is sometimes unnecessary to provide for additional signal analysis and correction of the basic QRST complex waveform exclusively for the purposes of determining the RR timing. Even with this stability, there are advantages to enhanced error detection, improved noise rejection and verification of the specific wave characteristics expected. It is a further object of this invention to enable enhancements in these validations of the base RR interval determination.

This additional analysis is valuable to provide for the confirmation of viable heartbeat (HB) and HRV data and to determine consistency and viability of the assessment.

It is an object of this invention to not only provide enhanced HB and HRV determination via the previously described methods, but to also enhance the assessment of the viability of the previously ascertained data and the associated determination. This capability is possible, without computing load penalty, via the below mentioned approach to the determination of a local slope surrounding the trigger point for the HB/HRV determination.

Figure 5:
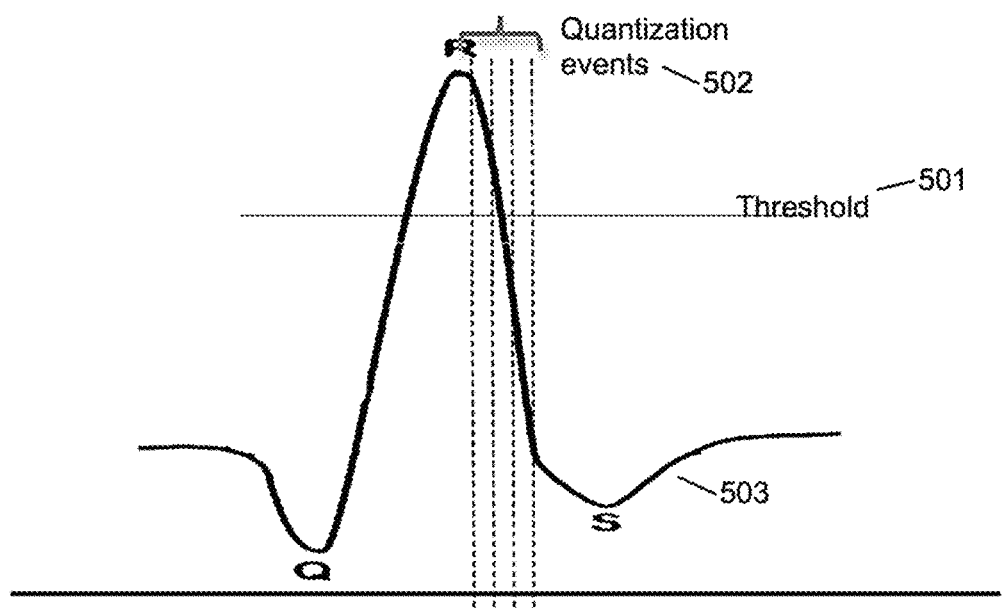
FIG. 5 shows signal threshold and surrounding QRS complex values.
Figure 6:
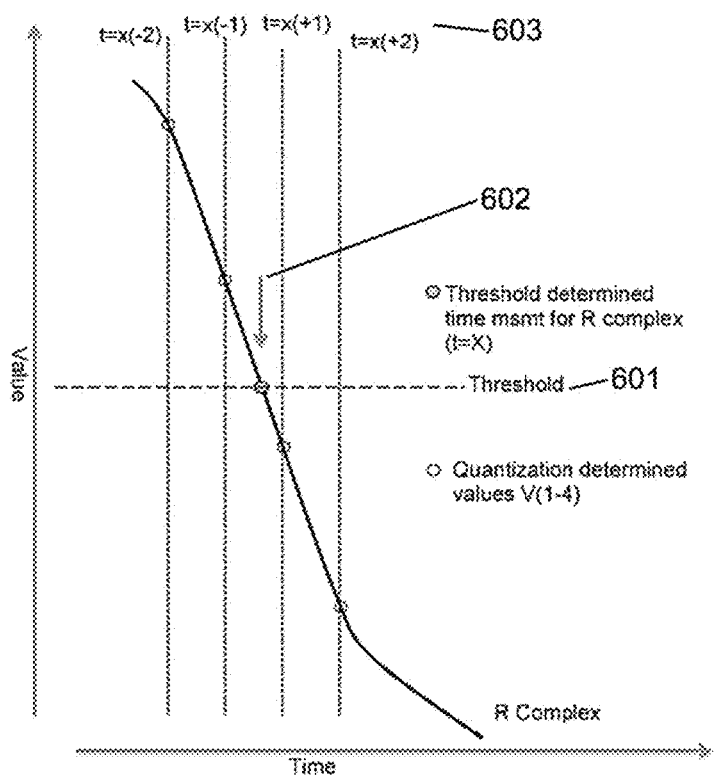
FIG. 6 shows a magnified view of the R complex, quantization values, and threshold value.

Referring to FIG. 5, a threshold method is utilized to analyze the QRS complex 503 and trigger an interrupt to determine HB and HRV. This previously described method, however, using the same trigger, is not limited to the use of this method for determining validity of assessment. A threshold 501 is used to determine the time value of a particular R complex (1). The quantization events 502 surrounding the threshold determined time value represent the QRS complex values at periods of quantization. Refer to FIG. 6 where a detailed view is provided.

A threshold 601 is used to determine the precise value for a time 602 determination of a temporal heartbeat for use in HRV. Surrounding the threshold value, as depicted by V(time=x(−2)), V(time=x(−1)), V(time=x(+1)), and V(time=x(+2)) 603 are quantized values for the R complex. Such quantized values may be used in the determination of a time value for the R complex heartbeat, but, as described herein, the threshold value is determined by an analog comparison triggering a timer. The threshold 601 may be a predetermined value stored within the memory 308 or a dynamically set value constantly refreshed based on historic data, such as previous magnitude variation of the R wave value.

As part of this invention, upon detecting and triggering the threshold 601 determined heartbeat value 602, the r complex values of time=t−2, t−1, t+1 and t+2 603 are stored in memory 308 and related to the threshold HB time value (t=X) 602. To accomplish this, the previously determined values (i.e., for t=−2, t=−1, t=1, t=2) 603 are continuously saved in a pipeline architecture and drawn off of the pipeline as needed, such that only the relevant values surrounding t=X are saved. This saving and relating operation occurs in real time and is accomplished without heavy computational burden. It is important to note that any required number (limited to a lower limit of 2 points) are saved and related to the singular t=X value 602 for the time of that heartbeat.

A subsequent computational operation is performed to determine the efficacy of the t=X time value 602 by interrogating the values of the points represented by, in the example of using 4 points, t=X(−1), t=X(−2), t=X(+1) and t=X(+2) 603. While the analysis includes, but is not limited to, trending values over time, one embodiment of this invention would require the values to be monotonically decreasing over the course of t=X(−2) through and including t=X(+2). Further, limits (both minimum and maximum values) of differences between adjacent points can be assessed as an additional correctness check.

Figure 7:
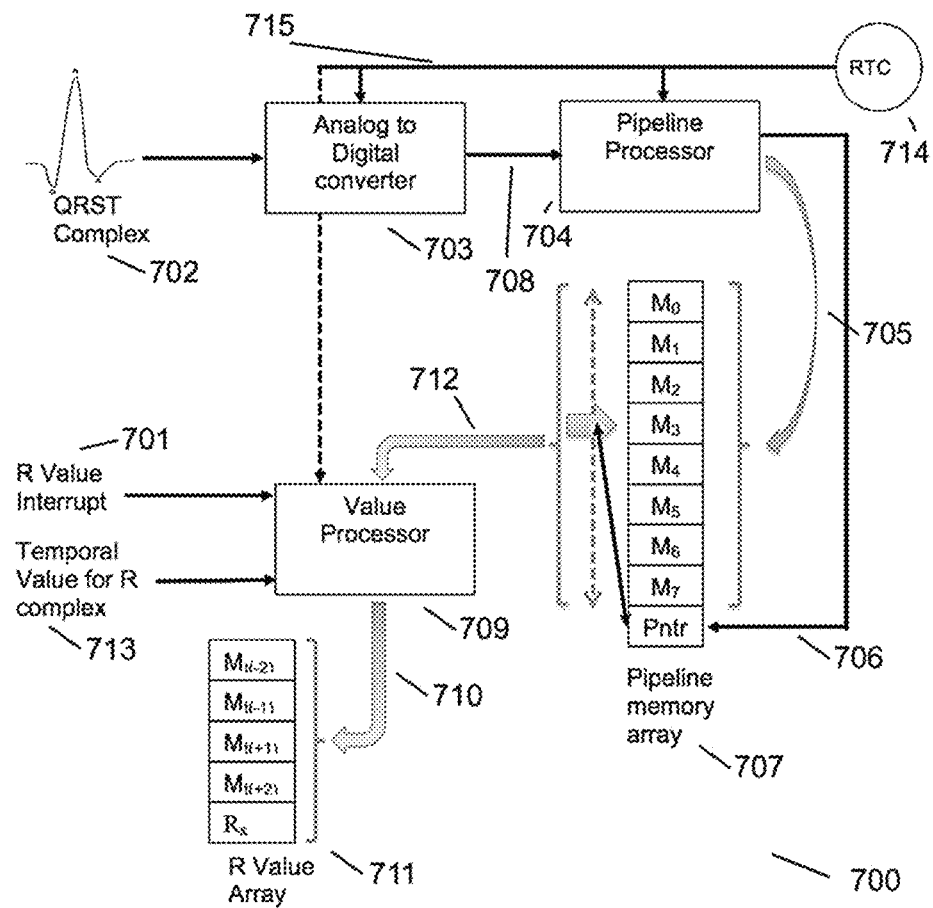
FIG. 7 shows a pipeline architecture for value determination and storage.

Referring to FIG. 7, a pipeline method is implemented for saving quantized values of specific interest for subsequent analysis, while using the analog threshold trigger to determine the heartbeat time value 701 via a microprocessor interrupt. This combination exerts no computational overhead for the system and provides for superb accuracy of the heartbeat time determination (eliminating interpolation), enables enhanced error and waveform examination, simultaneously without impacting real time performance. Other variations for saving quantized values localized to a point of interest may also be considered as being part of this invention.

For the above described threshold method, the processing method that is employed to determine specific values of the QRS complex 702 surrounding the threshold point 603 is operated as a pipeline such that surrounding values are determined and saved off with discretion on a real time basis. The QRST complex 702 is quantized 703 and a pipeline processor 704 serves to continually store 705 the quantized values 708 in a pipeline memory array 707. In some embodiments of this invention, the pipeline processor also maintains a pointer index 706 into the pipeline memory array, such that the start and end of the array is always identified. Upon trigger (i.e., via an R value interrupt 701), the at least two, but up to twenty values of the QRST complex surrounding the trigger point are stored 705 in memory 707. A value processor 709 transfers 710 both the values of interest 712 and the R value for the point of interest in a memory area as an R value array 711. The overall temporal value of each array set is maintained by the value processor 709, utilizing the temporal value for the R complex 713, to resolve any differences between individual R values and the originating QRST complex 702. These stored values can be used to determine the characteristics of the QRS complex at or near (i.e., surrounding) the trigger point and these characteristics validate the suitability of the assessed complex for HB, HRV and application assessment. A real time clock 714 can be used to sync 715 the quantized QRST complex and the value selection of the value processor.

In some embodiments, the described pipeline method 700 is used. In other embodiments, other designs of a pipeline process are used or other methods are employed. Other methods include full quantization of the entire QRST complex and relating this capture to temporal based identification of a point of interest, partially quantizing the QRST complex and relating these data to temporal based identification of a point of interest, or a full quantization of the QRST complex and subsequently identifying a point of interest and an associated locally relevant data set. It is not the intent of this invention to limit the value capture to the described methods, but to include all methods of capturing localized quantized data relevant to a specific point of interest for subsequent analysis.

While it would be clear to one skilled in the art that it is common for the input stream (the QRST complex) to be quantized and subsequently analyzed, this approach requires several design compromises not affecting the current invention. Specifically, processing speed, memory and power requirements for the rapid determination of values and subsequent analysis are needed, and it is incumbent upon a design to support sufficient error handling and detection and quality confirmations. The current invention minimizes the processing, memory and power requirements to determine the heartbeat temporal value, saves the relevant surrounding data, and, as further described herein, provides the opportunity to enhance the signal processing, error trapping and elimination and create a far more robust method for HRV determination while maintaining a very small computational profile.

In some embodiments of this invention, it is possible to utilize multiple inputs of a common signal to generate more robust capture of the QRST complex and determine the RR intervals.

Figure 8:
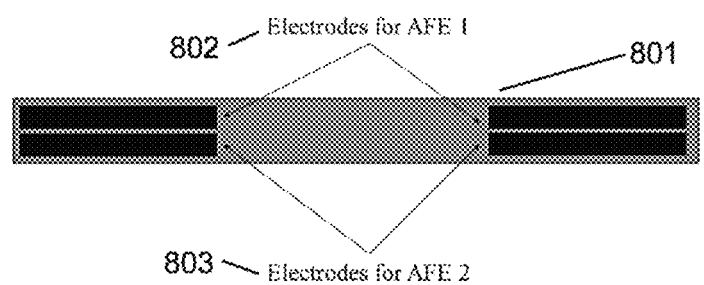
FIG. 8 shows a multiple contact chest strap for a one lead ECG.

FIG. 8 shows a multiple contact chest strap for a one lead ECG. The multiple-contact chest strap has improved resistance to the varying conditions of the contact to body connection. The chest strap 801 comprises an integrated first ECG analog front end (AFE) electrode (AFE1) 802 and a second AFE electrode (AFE2) 803. This integrated electrode approach provides increased robustness in the contacting and acquisition of the QRST complex and address variability in contact often experienced with single, non-redundant contact approaches. This approach is not limited to the depicted two redundant contacts, but may consider many multiple contacts and can further employ averaging, voting or other methods to obtain a robust signal.

Figure 9:
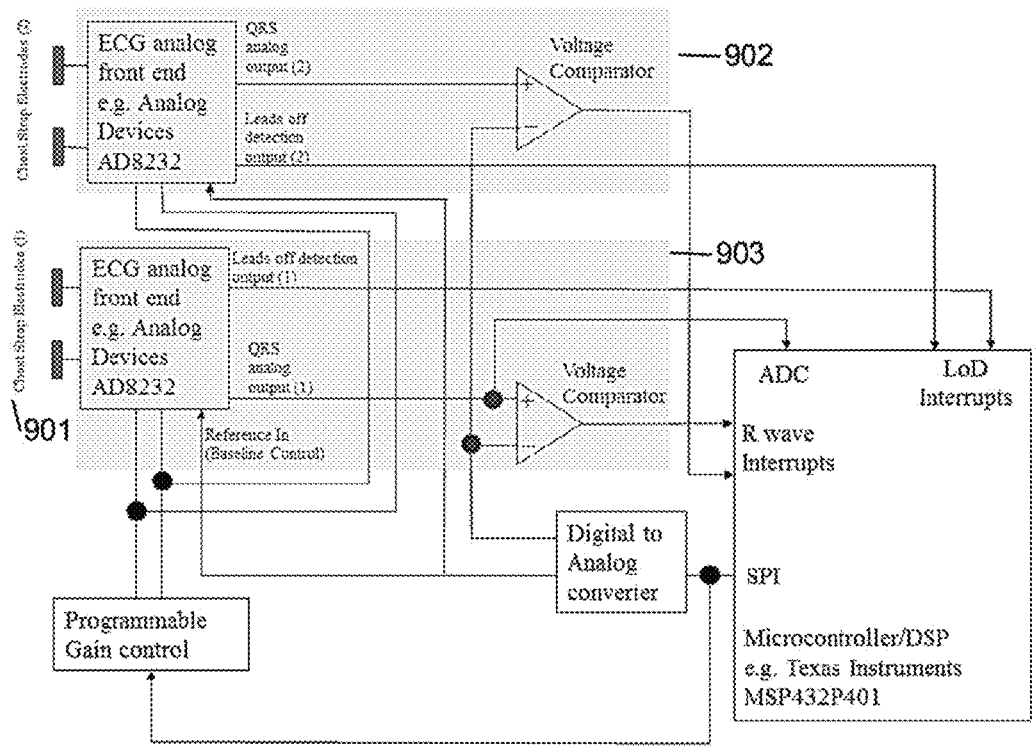
FIG. 9 shows a detailed block diagram of a multiple contact, single lead ECG front end.

FIG. 9 shows a detailed block diagram of a multiple contact, single lead ECG front end. The modified signal input and front end processing is depicted for a one-lead, two contact (901a and 901b) embodiment of the invention. This invention includes, but is not limited to two contacts, and may include as many multiple contact redundancies as found beneficial to reduce contact impact on signal noise and variability. Multiple contacts 901 are interfaces through redundant front end process interfaces 902. The one contact interface 903, as depicted earlier, remains intact.

In other embodiments, even those not employing a described threshold method, capturing the discrete points defining the determined HB and HRV values allows for the validation of these values. While more computationally intense and potentially not providing real time feedback, the validation remains as a valuable assessment of proper determination of HRV.

Determining HRV

Figure 10:
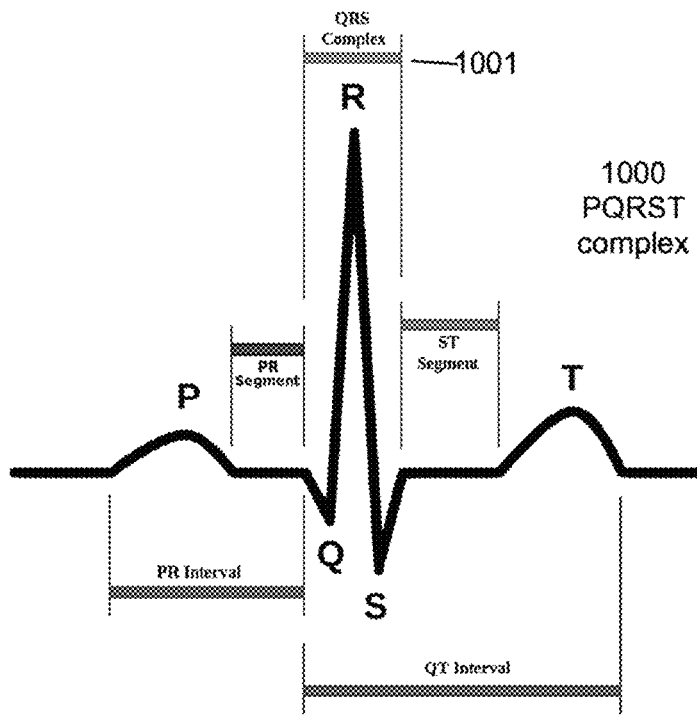
FIG. 10 depicts a PQRST signal complex.

Referring to FIG. 10, the device, via a detection capability, may use optical, electrical, or sonic methodologies, to detect heartbeats, and determine the subjects' RR intervals. In order to calculate HRV, the device must first capture a series of the time intervals between successive heartbeats. These are known as RR Intervals, since it is the time intervals between the R waves in the PQRST complex 1000.

The most common technique for detecting the QRS complex 1001 is to use an electrocardiogram, which uses one (a pair) or more electrodes to monitor the electrical activity that stimulates the heart. This technique, which can be miniature enough to be wearable, is described in various documents and is considered common practice with the current state of the art.

In addition, an optical, photoplysmography (PPG) technique has been shown to be able to extract RR intervals with sufficient accuracy, see Blake, "Development of a Bluetooth 4.0 photoplethysmography sensor for use in heart rate variability analysis".

Other techniques using pressure sensors or microphones can also be used to detect heart beat signals and subsequently extract RR interval duration as described in prior art "Efficient Heart Rate Monitoring" Sanjeev Kumar, Applications Engineer, Cypress Semiconductor Corp. Further, Optical imaging of a human body (face) via cameras can also be used to detect heart beat. The present invention can apply to, is not limited to and includes the use of any of these means for heart beat detection.

Figure 11:
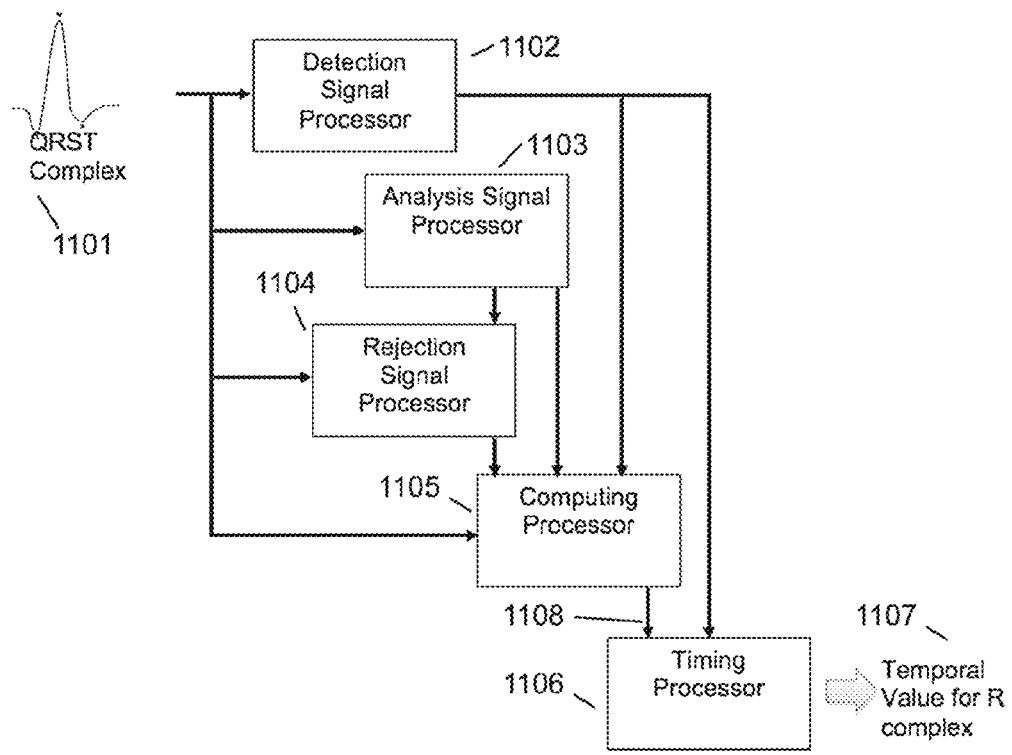
FIG. 11 is a processor block diagram for determining R temporal values.

FIG. 11 shows a processor block diagram for determining R temporal values. A series of processors to determine a valid R time value in determining R-R intervals. The processors in FIG. 11 may be a hardware processor, a software processing block, or a combination of both. A detection signal processor 1102 is used to determine the signal validity of a presented QRST complex 1101. This detection processor 1102 validates the overall characteristics of the QRST signal 1101 and determines if a suitable complex waveform is presented.

An analysis signal processor 1103 is used to perform the previous stated analog analysis, determining that an appropriate threshold crossing has been detected. This analysis supports the identification of threshold characteristics of an R complex.

A rejection signal processor 1104 examines the QRST complex 1101 and the associated candidate threshold crossing for the absence of it being ectopic. A computing processor 1105 combines the input from the detection signal processor, the analysis signal processor, and the rejection signal processor and assesses the candidate QRST complex 1101 for acceptability.

A timing processor 1106, triggering on the output of the analysis signal processor 1103 and a positive computing processor output 1108, captures the candidate R complex timing information 1107. This information is saved into memory for subsequent use.

In some embodiments, the above processors are comprised of discrete components, individual microprocessors, microcontrollers or PGAs, a single microprocessor, microcontroller or PGA, or a mixture of the above embodiments. The intent of this invention is not to limit the implementation of these processors, but to state the roles and needs for them.

Figure 12:
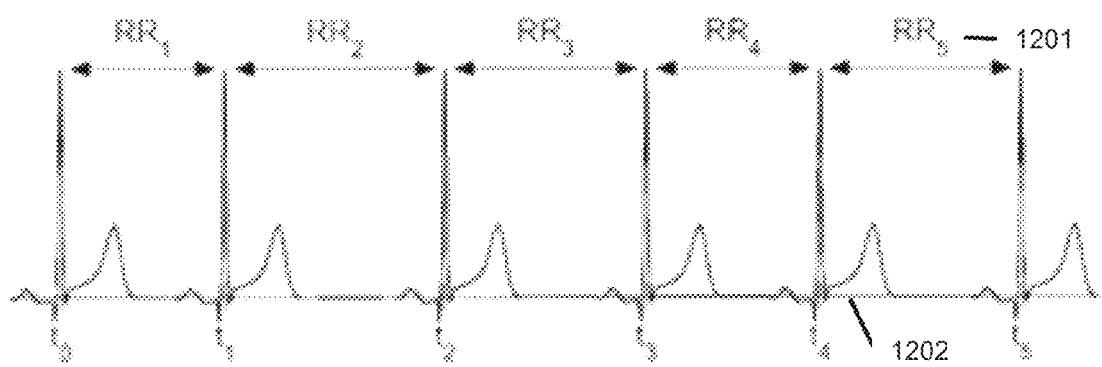
FIG. 12 shows R-R Intervals derived from PQRST complex signal.

FIG. 12 is an exemplary drawing showing R-R intervals. The RR interval values 1201, derived from the PQRST complex signal 1202, are loaded into a memory, such as the memory 308 or storage integrated within an onboard computation capability such as a microcontroller, microprocessor, or DSP. The computational device calculates the value the relevant HRV measurement(s), including those utilized for real time validation of the signals, real time validation of the quality of the critical heart rate determination, and HRV.

Figure 13:
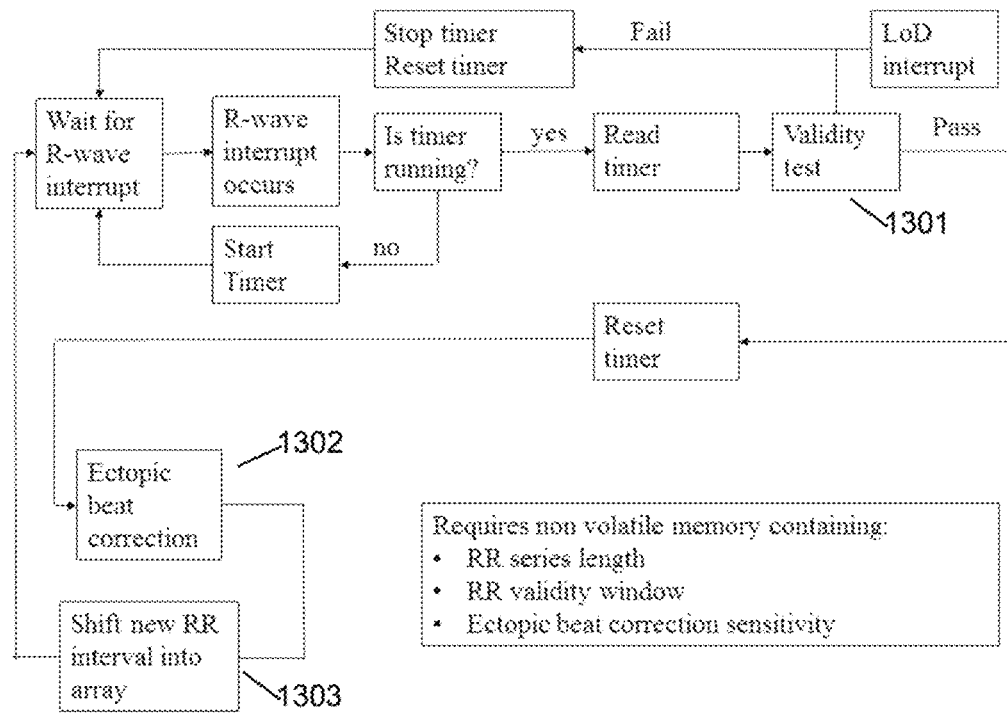
FIG. 13 is a logic flow diagram for determining valid R-R intervals for HRV.

FIG. 13 shows an exemplary logic flow for determining valid R-R intervals for HRV (signal reduction, processing, and analysis). By its nature, HRV is very sensitive to erroneous data. Before inserting a new value in the array 1303 it is necessary to validity check 1301 the new value. This is achieved by checking the value is within a plausible range for human beings 250 mS to 1400 mS. In addition, the value is tested against a 'window' around the mean value of the local dataset and if it falls outside the window the value may be discarded. Further, a check or identification for ectopic heartbeat 1302 is performed and used to qualify the signal prior to acceptance.

Figure 14:
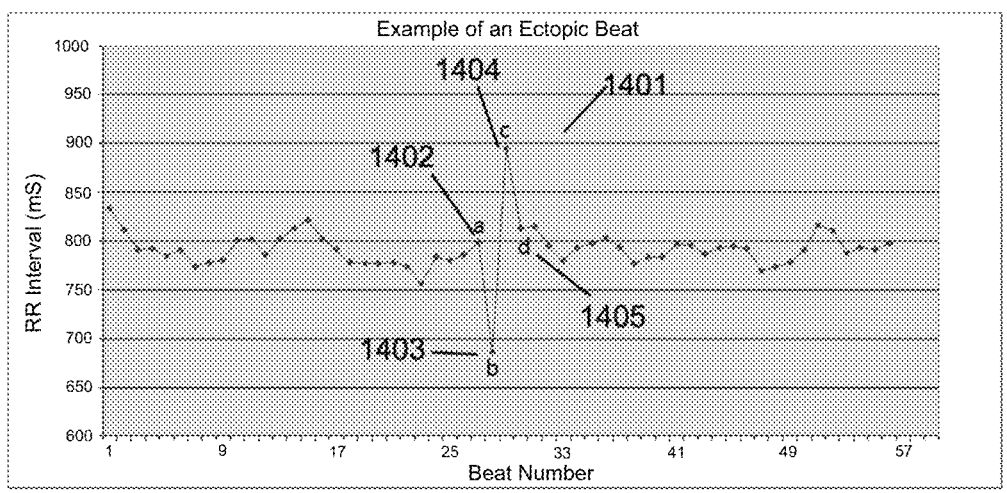
FIG. 14 shows a plot of ectopic heartbeat R-R intervals.

As stated, in addition to validity testing, data comprising RR intervals can be corrupt due to the presence of ectopic heartbeats. Referring to FIG. 14, an example of an ectopic beat 1401 (in an RR interval series) is shown.

If allowed to remain uncorrected, the RR values associated with an ectopic beat will significantly perturb the HRV measurement until those RR values have flushed from the parameter calculation array. The present invention features a novel method for detecting ectopic heartbeats and removing them from HRV determination consideration.

Figure 15:
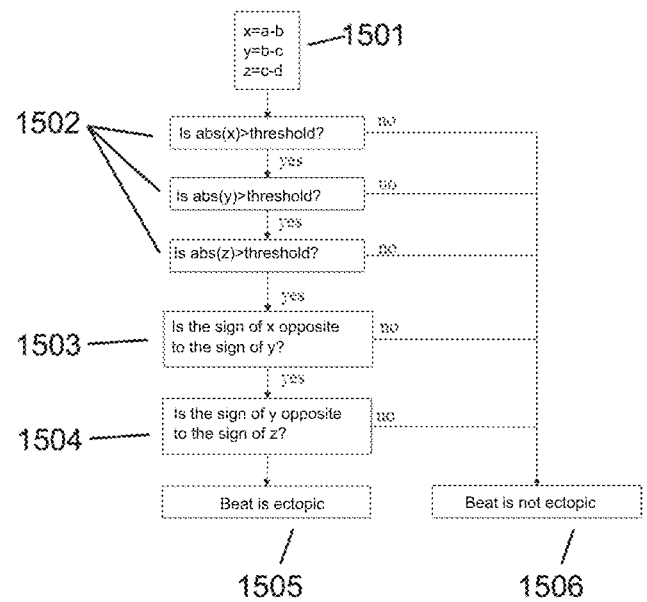
FIG. 15 shows a logic flow for an algorithm for detecting ectopic beats.

Referencing FIG. 14 and FIG. 15, intermediate values 1401 are determined from heartbeat values. An X value is calculated from the difference of adjacent heartbeats a 1402 and b 1403. A Y value is calculated from the difference of adjacent heartbeats b 1403 and c 1404, A Z value is calculated from the difference of adjacent heartbeats c 1404 and d 1405.

A series of tests are conducted to determine validity (i.e., non ectopic) of the heartbeat. In step 1501, a set of three adjacent heartbeats differences (X, Y and Z) are loaded. In step 1502, threshold tests for each of X, Y and Z are performed to assess the acceptability of the subject heartbeats relative to their R-R interval value short-term changes against a minimum difference threshold. An instance of the series of R-R intervals short-term change exceeding the difference threshold indicates a possible ectopic condition. The difference threshold can be a hardcoded (or predetermined) value or a user settable parameter. If any one of the three adjacent heartbeats differences is below the difference threshold, then the heartbeat is not ectopic in step 1506.

If all the three adjacent heartbeats differences are above the difference threshold, a second series of tests is performed in step 1503 and step 1504 to examine the change direction of adjacent heartbeat R-R intervals. This second test is examining that adjacent pairs of R-R intervals are monotonic at the series of interest. To be considered ectopic, multiple pairs of R-R interval differences surrounding a point of interest must be non-monotonic.

Figure 16:
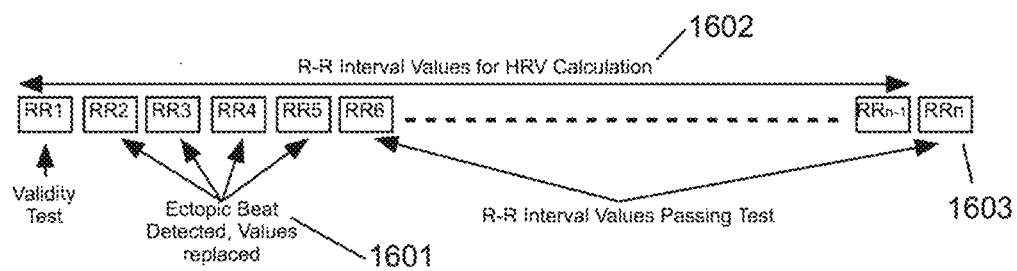
FIG. 16 shows a diagram of an R-R interval data set depicting the selection of values for HRV calculation.

Once an ectopic beat has been identified or detected 1505, referring to FIG. 16, the RR intervals with exceptional values 1601 are discarded completely, replaced by a predetermined value (such as the mean of the dataset) or replaced by interval values interpolated between the adjacent valid values. A resulting dataset (or RR interval array) 1602 is formed and used for HRV determination. The depicted dataset is shown diagrammatically.

Once a value for a new RR interval is considered valid all the elements of the array are shifted one place to the right and the value of RRn 1603 is discarded. The HRV measurement calculation is then initiated.

HRV Measurement Calculation

The selected HRV measurement(s) are calculated using the principles outlined in: Heart rate variability—Standards of measurement, physiological interpretation, and clinical use, European Heart Journal (1996) 17, 354-381.

In the interests of computational efficiency, however, the spectral parameters may be calculated using an autoregressive technique such as the Burg Method. Further, additional parameters may be calculated such as, but not limited to, nonlinear Poincare parameters SD1, SD2, SD1/SD2, described in Golinska, "Poincare Plots in Analysis of Selected Biomedical Signals". Also, entropy parameters such as Approximate Entropy, Sample Entropy and Fuzzy Entropy may be appropriate for some applications, the techniques are described in Chen et. al "Measuring complexity using FuzzyEn, ApEn, and SampEn".

These calculations are executed on the series of the most recent RR interval values. The size of the array is selectable between 60 and 600 samples, sampling at the smaller array size end of the range results in a faster response to change while sampling at the larger array size end of the range will result in greater accuracy of the calculated parameter(s).

Without wishing to limit the present invention to any theory or mechanism, the present invention may not only support the determination of HRV via a settable array size for analysis, but further, it may be advantageous to utilize multiple sampling approaches for HRV determination, using a smaller array size for rapid assessment and a larger array size for more accurate determinations. Such a sampling approach may be fixed, programmatically changed, or even dynamically adjusted to accommodate specific application requirements.

Figure 17:
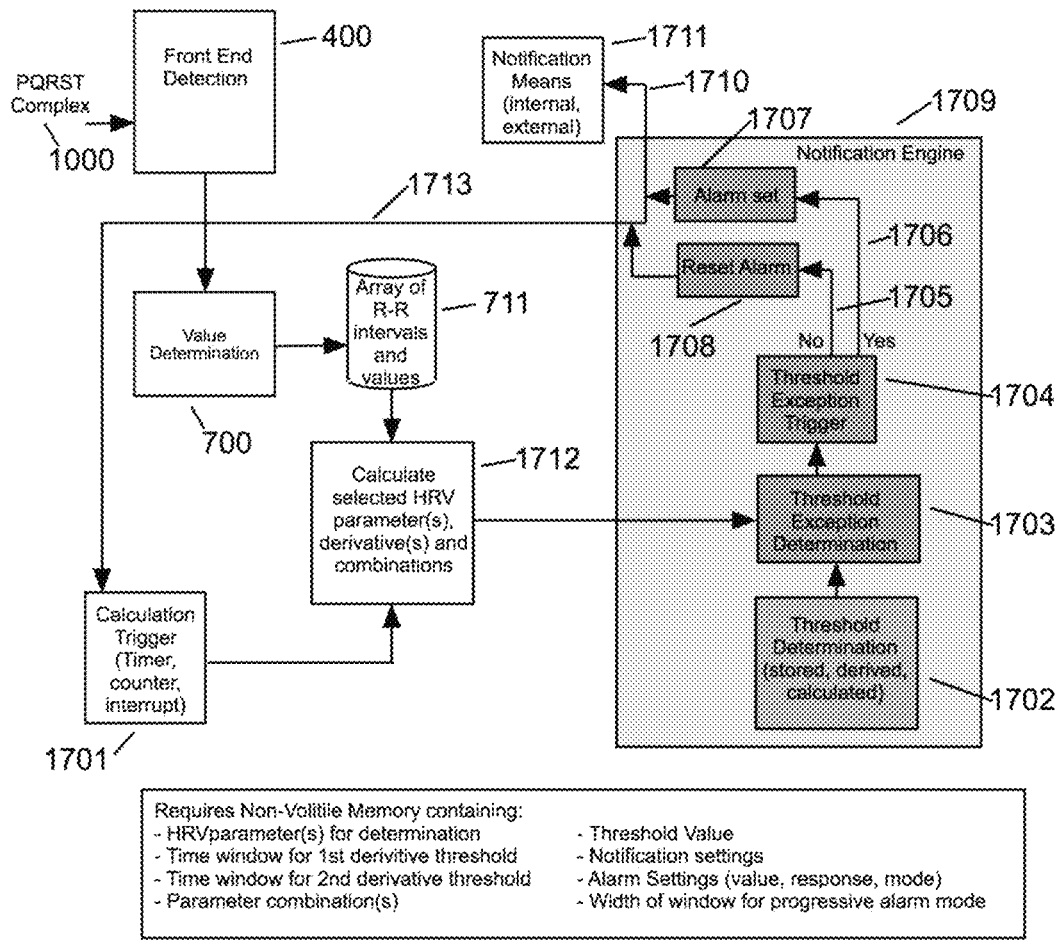
FIG. 17 shows a preferred embodiment of logic flow for determining HRV measurements.

FIG. 17 shows a preferred embodiment of logic flow for determining HRV measurements. The calculation of HRV measurement(s) may occur every time a new valid beat is detected, may occur by a pre-set period of heartbeats, may occur by a dynamically adjusted period to best fulfill an application's needs, or, in the interest of computational efficiency and power consumption, be initiated by a software interrupt every few seconds which can be user configurable. This is shown as the calculation trigger 1701.

As depicted in the preferred embodiment and previously described, the PQRST complex signal is processed via the front end 400 and an array of R-R intervals and the associated values of interest surrounding a determined R-R interval value is determined at step 700 and stored at step 711. At step 1712, at least one selected HRV measurement is calculated upon a calculation trigger 1701 is initiated. The trigger may be determined via a system timer, system event or via another form of software interrupt to initiates the calculation of HRV measurement(s), derivative(s) and combinations thereof from a predefined or dynamically determined group of parameters and pre-determined algorithms.

These values are based on analysis of the data in the R-value array 711. The HRV measurement may be a statistic parameter calculated from the array of R-R intervals. Examples of HRV related parameters are listed in the table shown in FIG. 2.

The figure depicts a specific embodiment of a logic flow for determining HRV measurements and the inclusion of a notification engine 1709 as part of the embodiment. This engine, in the preferred embodiment, provides for a determined (stored, derived or calculated) HRV threshold value 1702, an examination of HRV measurement(s) based on said threshold(s) and a determination of threshold exceptions 1703, and the setting, as necessary, of exception triggers 1704. These triggers 1705 and 1706 are maintained via alarm set 1707 or alarm reset 1708 flags. The determination of threshold exceptions 1703 and the triggering of a notification 1706 can be from derived, stored or dynamically calculated criteria.

In some embodiments, the HRV threshold 1702 can be obtained from pre-stored values, from derived values (e.g., from a combination of stored parameters and a defined algorithm) or ideally (for certain applications) from dynamically determined parameters, with threshold values calculated real time. An example of this would be HRV threshold(s) determined based on heartrate, activity, motion, and/or temperature.

As determined by notification settings, alarm status and the hardware of a specific embodiment for notification 1711, internal (i.e., self contained) notification or external (i.e., remote—wired or wireless) notification is available. Completion of this logic and a reset 1713 sent to the calculation trigger 1701 restarts the process.

While this is a specific embodiment of the described invention, this embodiment is not meant to limit the logical flow, nor is this embodiment meant to limit the notification methods, to limit the acquisition and determination of HRV values for the current invention. It would be clear to one skilled in the art that various modifications may be implemented to the logic flow disclosed in FIG. 17 to realize similar HRV measurement determination and notification generation function. Such variations are within the scope of this invention.

It should be noted that depending upon sampling size (i.e., duration and/or count of R-R interval determination), the effectiveness of error detection and error correction and the technique employed, certain approaches to determining a real time, versus a baseline or long term HRV are more optimal than others. Further, it can be advantageous to create and analyze a comparison of baseline versus short term HRV as part of this invention. It further can be an advantageous to create and analyze changes in HRV (e.g., rate of change) in short term versus long-term conditions. An advantage of this invention is that it enables the determination, trapping and correction of errors, while minimizing the computational and power overhead required for these operations. This provides the opportunity to establish highly robust short-term HRV determinations—crucial for many applications of HRV.

FIG. 18 shows a table of HRV applications, associated parameters and relevant criticality. The table provides examples of some specific applications and the associated applicable HRV measurements and other parameters. This invention includes, but is not limited to, the stated examples and it is intended that this invention includes all combinations of the incorporation of at least one other parameter with HRV to provide an assessment to the user.

The present invention also features methods for determining status, notifications and/or alerts based on HRV and potentially other real time monitored parameters. The method may feature (a) the absolute value of a selected HRV measurement; (b) the rate of change of a selected HRV measurement (1st derivative, 2nd derivative, etc.) or a combination of these for one or more HRV measurement(s); (c) heartrate and or respiration rate/body temperature and/or the associated rate of change of any of these parameters; (d) the notification may be automatically modified by inputs from optional onboard sensor(s), comprised of, but not limited to, an accelerometer, a gyroscopic sensor, a GPS, an EEG, or an electrodermal activity monitor; in order to clarify changes in HRV resulting from but not limited to exercise or other physical activity; (e) the user may be notified to a change in their physiology through a variety of permutations of HRV measurement value(s) and other sensed parameters.

By virtue of its flexibility in terms of automatic gain setting, baseline setting and threshold detection setting, the capability of the preferred embodiment of the invention may, in addition to measuring the time between successive R waves, be designed to measure other periods within the PQRST complex. An instance of this, to which this invention includes but is not limited to, is the period between Q and T, known as the QT interval. It is understood that this interval and its variation (known as QT dispersion) has clinical application in some medical conditions such as sleep apnea and ventricular arrhythmias. The QT interval and/or dispersion may be combined with HRV measurements and other QRST parameters such as PR interval or PR dispersion to refine the accuracy of a notification or create new notifications based on the variations of the various timing, combinations and/or permutations within the QRST complex.

In the event that heart rate variability changes in a way that is pre-defined for the user's condition and other parameters, the user is notified to this change. Pre-definition includes, but is not limited to: programmable parametric values based on user historical collected data; varying number of RR intervals used for parameter calculation; multiple application areas combined in a single user profile, set-up, response parameters; defining multiple notification and alerting techniques; using many different HRV measurements in isolation or combination; incorporating other parameters, including, but not limited to motion detector to monitor user activity; determining user's body position (e.g., lying down or sitting/standing); incorporating temperature (monitor user's body temperature, environmental temperature); Incorporating barometric pressure (determining user's altitude and/or altitude changes); saving data externally for subsequent analysis; and/or obtaining and using data from other external devices (e.g. blood pressure).

Notification, Alerting and/or Providing Status to User

Using the determined data and optionally, pre-determined parameters and limits for an individual, the subject may be notified to the proximity to their dynamically determined (using pre determined and dynamic parameters) threshold via a user notification means, to include but not be limited to: a haptic indicator via a motion-generating component (e.g., vibrating, pulsing, translating); an audible indicator via a sound-generating component (e.g., loudspeaker, earpiece, piezoelectric transducer); a visual indicator via an optical component (i.e., an LED, LCD, OLED, graphic display, or other visual indicator providing indication via color modulation, color differences, light intensity, light modulation); A mild electric impulse to the body (e.g., mild electric shock);

A direct, nervous system indicator (e.g., brain bio-feedback connection); or any combination of the above.

All of the above may be presented to the user via the invention, being one of a visibly available body mounted device (i.e., appendage mounted, ocular, aural, clothing design for visible indication of information); a non-visibly available body mounted device (i.e., a chest strap or patch, an appendage strap or patch, clothing design for the purpose of allowing for non-visible indication of information); a portable, non-body mounted device (i.e., a display mounted on equipment utilized by the user, the user's support or care team, or a commissioned professional).

In some embodiments, the notification or alerting method may be user selectable as absolute or progressive, e.g., in the case of haptic feedback, if the user has selected 'absolute' the device may vibrate constantly whenever the selected threshold is exceeded. In the case of 'progressive', the device may vibrate gently as the threshold is approached, moderately when the threshold is reached and violently if the threshold is exceeded.

Alternate System Embodiments

Figure 19:
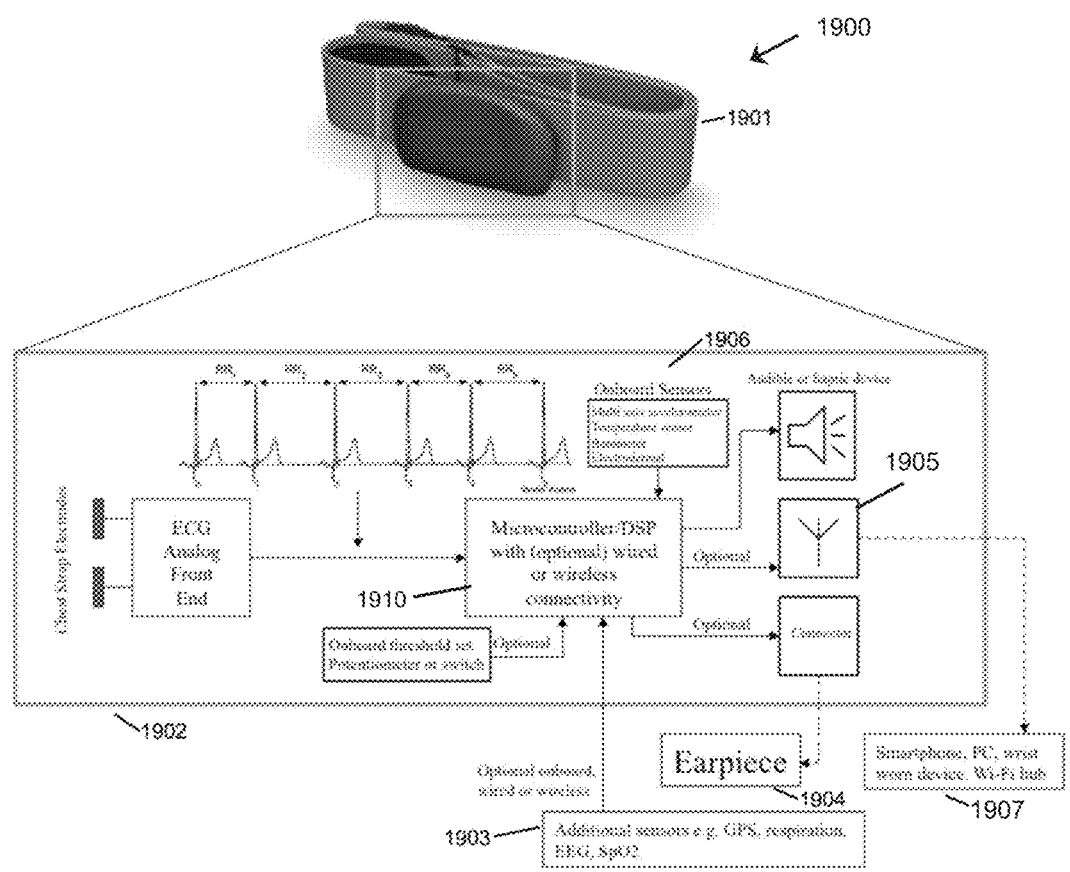
FIG. 19 shows an example of a HRV monitoring system of the present invention, fully integrated into a single device.

Referring to FIG. 19, a fully integrated, self-contained, battery powered, portable Wearable Physiological Monitor (WPM) device 1900 is depicted. The device is configured to incorporate HRV detection, user desired assessment, and, in situ user notification, in real time. The device comprises a chest strap 1901 and a processing circuit 1902.

In some embodiments, the device incorporates additional on-board sensor 1906 and wireless communication interface 1905 to communicate with external devices 1907, such as smartphones, smart watches, wireless connections, personal computing devices. The device may further be configured to receive input from external sensors 1903, such as a GPS sensor, a respiration sensor, a $SpO_2$ sensor, etc. The on-board sensor 1906 or the external sensors 1903 may be a sensor for acceleration, gyroscopic detection, temperature sensing, barometric pressure measurement and/or electrodermal activity identification. The on-board sensor 1906 and/or the external sensors 1903 couple to a microprocessor 1910 within the processing circuit 1902 such that the microprocessor 1910 receives at least one additional input (from the on-board sensor 1906 and/or the external sensors 1903) unrelated to the QRS waves detected by the one or more electrodes. The additional input may be related to acceleration, rotation, orientation, user temperature, barometric pressure, electrodermal activity, respiration rate, a user-specified input, a previously specified parameter, etc.

Figure 20:
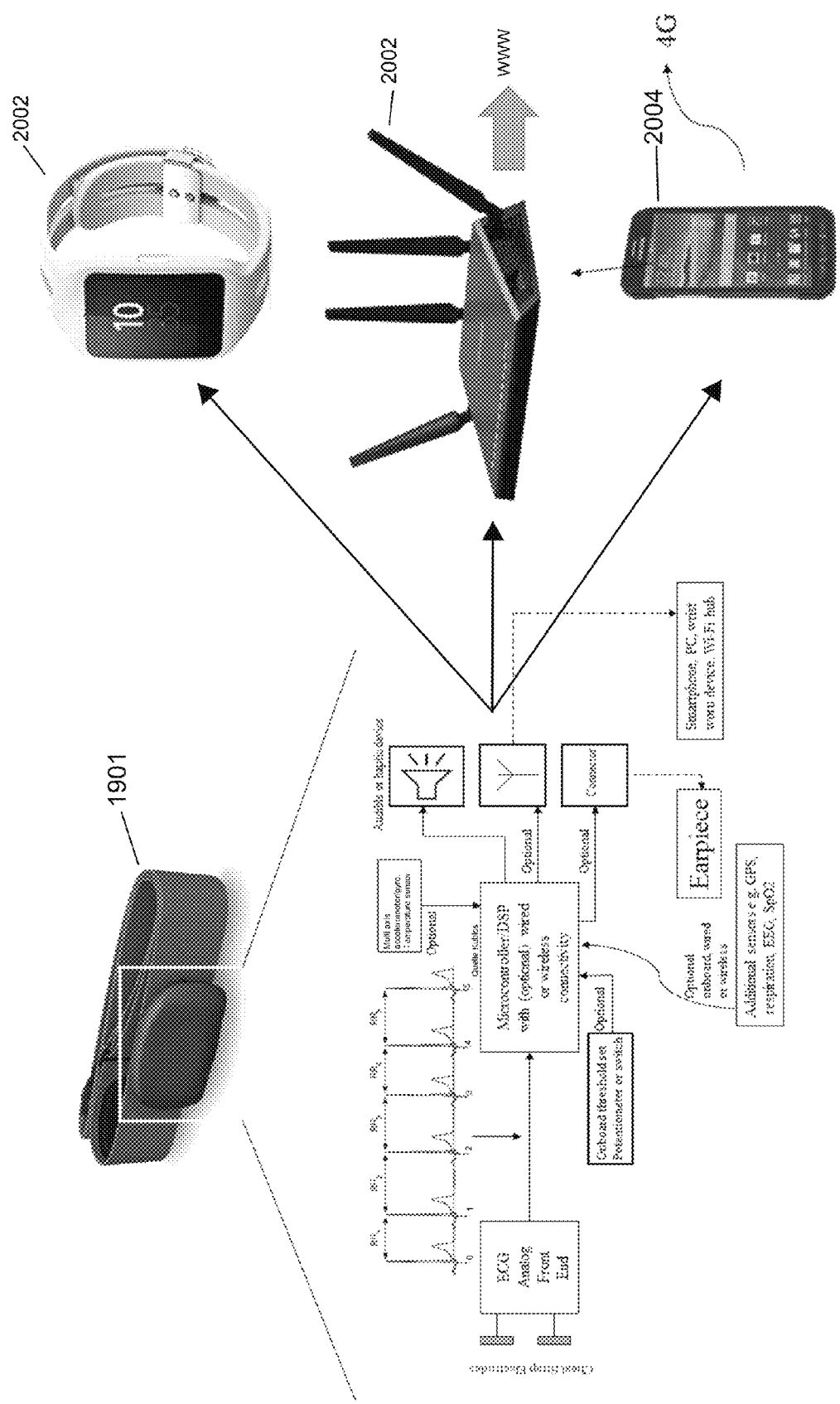
FIG. 20 shows a diagrammatic view of system connectivity (i.e., the Wearable Physiological Monitor (WPM) with external connectivity and devices).

Referring to FIGS. 19 and 20, to further explain the above-mentioned connectivity, in addition to an embodiment as a standalone wearable physiology monitor (WPM) 1900, the device may be used within a network through the on-board wireless communication interface 1905, which may be configured to support various available wireless communications protocol (either standards based or proprietary). These protocols may include, but are not limited to Bluetooth, Ant, Wi-Fi (802.11) 2003, cellular connectivity 2004, XBee™ and Zigbee™. Further, other devices, such as a smart watch 2002, a smart phone 2004, or a remote connect PC or tablet computing device (via wireless 2003 or wired 1903 connectivity) may be utilized to couple to the device 1901 to receive notification, download RR interval data array, send user selectable input, etc.

The connected peripherals may be used as notification and/or alerting devices, may optionally include some or additional computation capabilities, for example, threshold detection, and may optionally also be used to forward all or selected elements of the transmitted data onwards for remote notification, alerting, monitoring or offline storage and analysis. This invention describes the scope of such system(s), recognizing that specific configurations are dependent upon optimization for user needs, the intended use of the system, and the specific application(s) being addressed.

Applications

It is through the system analysis of user needs, the intended use of such a herein described system and through specific assessment of applications that a final system configuration manifests.

As an object of this invention, the self-contained, portable, battery powered device herein described provides one level of utility for a user. By combining this device with additional, integrated system components, additional utility is realized.

By providing connectivity, the system extends the utility of the device by enabling third parties to be remotely alerted for events or episodes of interest, including but not limited to: a team coach monitoring his players; the manager of an air traffic control team; patient care team and a patient's physician; parents of a child with a chronic illness.

Figure 21:
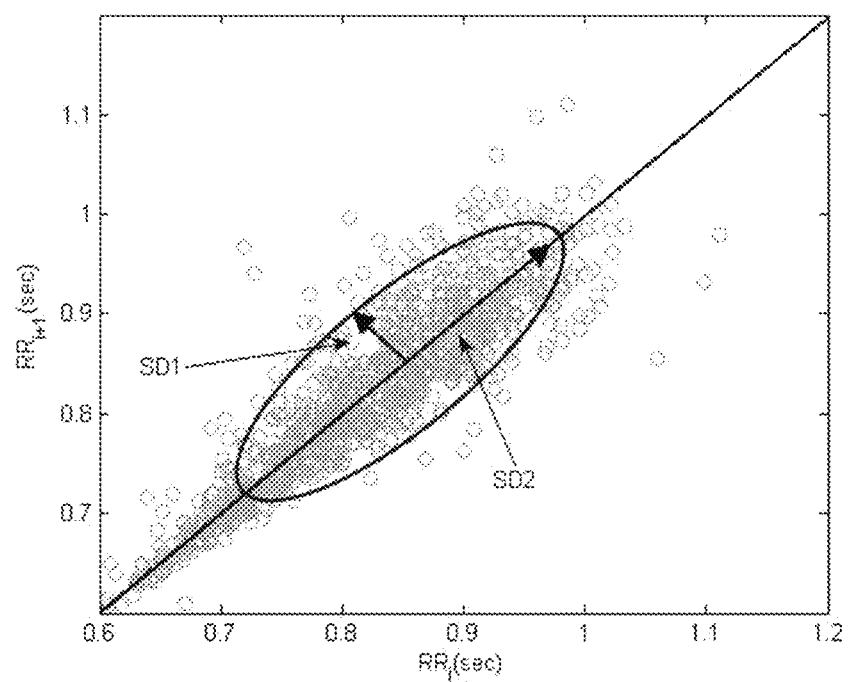
FIG. 21 shows an exemplary Poincare plot for RR interval to define HRV measurements SD1 and SD2.

Some examples of the application of this invention, including but not limited to the disclosed use cases are:

An Example Non-clinical application of the device—Endurance Athletics: The HRV measurement SD1 has been widely reported to be a good indicator of the onset of lactate threshold as exercise intensity increases. Determination of Anaerobic Threshold by Heart Rate or Heart Rate Variability using Discontinuous Cycle Ergonometry, Park et al, International Journal of Exercise Science 7(1): 45-53, 2014. As exercise intensity increases, SD1 begins to fall from a value of around 16 to, at maximum intensity, a value less than 1.0. In endurance athletics it is crucial that the athlete remain below their lactate threshold in order to be able to maintain a sustainable power output. The device would be configured to determine SD1 and progressively alert the subject as the value approaches 3.0 (the generally accepted value corresponding to lactate threshold). This would allow the subject to reduce their output until the alert has been eliminated and enable the subject to continue at maximal aerobic output. In endurance athletics it is crucial that the athlete remain below their lactate threshold in order to be able to maintain a sustainable power output. FIG. 21 shows an exemplary Poincare plot for RR interval to define the HRV measurement SD1 and HRV measurement SD2 (FIG. 21 is cited from FIG. 1 of article "Complex Correlation Measure: a novel descriptor for Poincaré plot" by Chandan K Karmakar, Ahsan H Khandoker, Jayavardhana Gubbi, and Marimuthu Palaniswami, BioMedical Engineering OnLine, 2009, 8:17). The Poincare plot is an X-Y plot of the most recent RR Interval vs the previous RR Interval. Typically, the plot for healthy individuals generally forms an ellipse. The minor axis of the ellipse is known as 'SD1' and the major axis 'SD2'. As exercise intensity increases, SD1 begins to fall from a value of around 16 to, at maximum intensity, a value less than 1.0.

Other non-clinically oriented applications may include, but are not limited to: stress management; driver fatigue monitoring and alerting; mood changes and mood management; impending SIDs event detection and alerting; athletic recovery (from training or injury).

An Example Clinical application of the device—Epileptic seizure prediction:

"Pre-ictal heart rate variability assessment of epileptic seizures by means of linear and non-linear analyses", Anadolu Kardiyol Derg 798 2013; 13: 797-803. This publication demonstrates that the spectral HRV measurement LF/HF and SD1/SD2 both increase abnormally in the minutes leading up to a seizure with the values of both increasing by more than 80% during the final 5 minutes. By configuring the WPM to respond to a rate of change of (LF/HF and SD1/SD2) greater than 20% in 2 minutes would result in the patient becoming aware of their impending seizure about 3 minutes before the event actually occurs.

Other clinically oriented applications include, but are not limited to: Patient chronic illness; Cardiac patient care; Mental illness—diagnosis, treatment, monitoring; Diabetes monitoring; Sleep apnea; Discord between QRS determined HRV (ECG) and hydrodynamically determined (e.g., Photoplethysmography) HRV as compared to ECG determined HRV.

Means of Setup

As an element of the herein taught invention, attention has been invested in improved methods for the setup and use of such a system. These areas include: How to select an alerting parameter threshold; Use of a potentiometer mounted with the wearable device; 'Up/Down' pushbuttons mounted on the wearable device. Alternative means: Via wired of wireless connection from a smartphone, tablet or PC (personal programmable device—PPD). The PPD runs an application, which allows the user to select the required parameter(s), nature of the threshold (e.g. absolute value, 1st derivative, 2nd derivative and value of the threshold of those selected parameters. The PPD would also be able to change the ectopic beat detect threshold.

A more user usable application would be one that allows the user to select, using a menu, the required condition they wish to monitor. The PPD would then download the appropriate settings or even computational algorithm to the body worn sensor. A more exotic, personalized version of the application would have the user select the condition they wish to monitor, then put the user through a series of tests relevant to their condition, from which the PPD can 'learn' their HRV and other parameters and then determine thresholds specific to the user. While there are many potential embodiments of the herein described invention, the current preferred embodiment features the following novel approaches and improved capabilities over previously taught systems.

Programmable: The device may be configured to suit a particular application such that it can remain standalone and wearable, e.g., not requiring any other devices such as PC or smartphone.

In example, the device can vary the number of RR intervals used for parameter calculation: The size of the series may be varied during the programming process to suit the application and the user's needs. For instance, when using the HRV measurement LF, a longer series is required in order to capture all the components of the low frequency band. When used as a lactate threshold monitor and alert, a short series of RR intervals would be used in order to minimize the time to alert the subject of their impending situation.

Multiple application areas: By virtue of its small size and unobtrusive nature the device has a very wide range of areas of application from monitoring sleeping infants to warning active firefighters of over exertion, to monitoring of a team of Air Traffic Controller and distributing work to balance out stress.

Multiple notification techniques. The device can provide user notifications using audible, haptic, visual or electrical impulse techniques. In addition, using remote devices such as smartphone, smartwatch or PC, the user can be alerted. Further, the device and generate a notification, alert or generate data, which can be transferred to a central (e.g., cloud based) system and that system can transfer or generate notifications or alerts as appropriate.

Capable of using many different HRV measurements in isolation or combination: Much of the prior art relating to HRV, references HRV in a general sense without any specification of the HRV measurement(s) used. Where the prior art is more specific it generally references one HRV measurement such as SDNN or RMSSD. A unique element of this invention is that it has the capability to generate any or all of a full range of HRV measurements and use them either in isolation or in combination.

Incorporated motion detection to monitor user activity: When the monitor is programmed to alert a user who would normally be inactive, the device is capable, via its motion detection, of determining when the user starts moving around and how vigorous their activity is. This capability may be used to modify HRV thresholds appropriate to the activity of the user.

Determine user's body position e.g. lying down or sitting/standing: When activated for sleep monitoring, the motion detection and orientation detection within the device can determine if the subject is lying down, thereby avoiding false alarms associated with, for example, sitting up in bed.

Incorporated thermometer to monitor user's body temperature: When used, for example, for infant sleep monitoring, the measurement of the subject's body temperature has been shown to provide valuable additional information in determining appropriate alert conditions. The WPM can perform this assessment stand alone or in conjunction with other devices.

Incorporated barometer determines user's altitude: The vagal balance of the heart varies with altitude. The inclusion of a barometer in the preferred embodiment provides a means of compensating for this variation.

Small enough to be inconspicuously wearable: The total footprint of available integrated circuits to implement the device including auxiliary sensors, haptic feedback transducer and an optional Bluetooth radio module is 185 square millimeters. These would fit within the confines of the current preferred embodiment as well as available heartrate monitoring modules.

Self-contained, does not require external devices or power: The invention is unique in that its primary embodiment is entirely self-contained and requires no other devices for normal operation. This is important for those environments where a WPM application must be independent upon such external devices being present, available and in working order.

Low manufacturing cost: By virtue of the low component count and high firmware content, the device manufacturing cost will be low. This will enable high accessibility to the benefits of HRV monitoring to all classes of users.

Capable of saving data for subsequent analysis without external connectivity: The addition of optional onboard memory, in example, a micro SD card, enables data to be stored for subsequent analysis such as HRV trend identification.

Capable of obtaining and using data from other external devices, e.g., a blood pressure device: Bluetooth low energy wireless communication allows the device to communicate with the IoT and reconfigure based on input from external devices.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although as described in the preferred embodiment of the present invention, it will be readily apparent to those skilled in the art that modifications may be made thereto which do not exceed the scope of the appended claims. Therefore, the scope of the invention is only to be limited by the following claims. Reference numbers recited herein are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

We claim:

1. A wearable device for real-time detection, analysis and application of heart rate variability (HRV), the device comprising:
   a. a chest strap integrated with one or more strap electrodes to detect a plurality of consecutive QRS waves; and
   b. a battery-powered and self-contained processing circuit comprising:
      i. a microprocessor operatively coupled to the one or more electrodes and configured to receive at least one additional input unrelated to the QRS waves detected by the strap electrodes;
      ii. an ECG analog front end (AFE) circuit coupled between the microprocessor and at least one strap electrodes to provide a signal gain control to a strap electrode output such that the microprocessor receives signals with a desired amplitude, wherein the ECG AFE circuit has an internal amplifier where the internal amplifier operates to output a conditioned QRS signal comprising the plurality of consecutive QRS waves;
      iii. an analog voltage comparator coupled between the ECG analog front end circuit and the microprocessor, wherein the analog voltage comparator operates to detect one or more specified characteristics of the conditioned QRS signal, wherein the plurality of consecutive QRS waves, detected by the one or more strap electrodes, are received by the ECG AFE circuit wherein the internal amplifier of the ECG AFE circuit operates to convert the plurality of consecutive QRS waves into a conditioned QRS signal, wherein the conditioned QRS signal is received by the analog voltage comparator where the analog voltage comparator operates to detect the one or more specified wave characteristic of the conditioned QRS signal whereupon detection of the one or more specified wave characteristics, the analog voltage comparator triggers an interrupt directly to a signal processor integrated into the microprocessor;
      iv. a non-volatile memory storing computer-readable instructions that, when executed by the microprocessor, cause the microprocessor to perform operations comprising
         A. detecting a rising edge or a declining edge of an R-wave from each of the QRS waves;
         B. triggering an interrupt when the rising edge or the declining edge crosses a trigger point, the trigger point for interrupt triggering being predetermined or dynamically adjusted value;
         C. recording a time value each time when the interrupt is triggered;
         D. determining an RR interval each time when the time value is recorded;
         E. generating a temporal RR interval array, the RR interval array being stored within the memory and comprising a plurality of determined RR intervals;
         F. generating an HRV measurement based on the temporal RR interval array; and
         G. comparing the generated HRV measurement to an HRV threshold and outputting a real-time notification when the HRV threshold is reached, the HRV threshold being determined at least by the additional input unrelated to the QRS waves; and
      v. a notification means to receive the real-time notification to generate a user alert, the notification means being a haptic indicator, an audio indicator or a visual indicator.

* * * * *